US007888532B2

(12) United States Patent
Cho

(10) Patent No.: US 7,888,532 B2
(45) Date of Patent: Feb. 15, 2011

(54) TWO-PHOTON PROBE FOR REAL-TIME MONITORING OF INTRACELLULAR MAGNESIUM IONS, METHOD FOR PREPARING THE TWO-PHOTON PROBE AND METHOD FOR REAL-TIME MONITORING OF INTRACELLULAR MAGNESIUM IONS USING THE TWO-PHOTON PROBE

(75) Inventor: Bong-Rae Cho, Seoul (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 501 days.

(21) Appl. No.: 12/002,027

(22) Filed: Dec. 14, 2007

(65) Prior Publication Data

US 2008/0293088 A1    Nov. 27, 2008

(30) Foreign Application Priority Data

May 25, 2007    (KR) .................... 10-2007-0051131

(51) Int. Cl.
C07C 229/00    (2006.01)
C12Q 1/20    (2006.01)

(52) U.S. Cl. ............................. 562/455; 560/44; 435/29

(58) Field of Classification Search ................. 562/455; 460/44; 435/29
See application file for complete search history.

(56) References Cited

PUBLICATIONS

Kim et al, Angew. Chem. Int. Ed. 2007, 46, 3460-3463.*
H. Komatsu, et al., *Design and Synthesis of Highly Sensitive and Selective Fluorescein-Derived Magnesium Fluorescent Probes and Application to Intracellular 3D $Mg^{2+}$ Imaging*, J. Am. Chem. Soc., vol. 126, 2004, pp. 16353-16360.
G Farruggia, et al., *8-Hydroxyquinoline Derivatives as Fluorescent Sensors for Magnesium in Living Cells*, J. Am. Chem. Soc. vol. 128, 2004, pp. 344-350.
W. R. Zipfel, et al., *Nonlinear magic: multiphoton microscopy in the biosciences*, Nature Biotechnology, vol. 21, No. 11, Nov. 2003, pp. 1369-1377.
F. Helmchen, et al., *Deep tissue two-photon microscopy*, Nature Methods, vol. 2, No. 12, 2005, pp. 932-940.
R. M. Williams, et al., *Multiphoton microscopy in biological research*, Current Opinion in Chemical Biology. vol. 5, 2001, pp. 603-608.
R. Long, et al., *The Rigorous Evaluation of Spectrophotometric Data to Obtain an Equilibrium Constant*, J. Chem. Ed., vol. 59, No. 12, Dec. 1982, pp. 1037-1039.
K. Hirose, *A Practical Guide for the Determination of Binding Constants*, Journal of Inclusion Phenomena and Macrocyclic Chemistry, vol. 39, 2001, pp. 193-209.

B. Metten, et al., *Synthesis of APTRA Derivatives as Building Blocks for Low-Affinity Fluorescent $Ca^{2+}$ Indicators*, Synthesis, No. 11, 2005, pp. 1838-1844.
J. N. Demas, et al., *The Measurement of Photoluminescence Quantum Yields—A Review*, Journal of Physical Chemistry, vol. 75, No. 8, Apr. 15, 1971, 991-1024.
C. Reichardt, *Solvatochromic Dyes as Solvent Polarity Indicators*, Chem. Rev. vol. 94, No. 8, 1994, pp. 2319-2358.
H. A. Benesi, et al., *A Spectrophotometric Investigation of the Interaction of Iodine with Aromatic Hydrocarbons*, J. Am. Chem. Soc., vol. 71, 1949, pp. 2703-2707.
G Grynkiewicz, et al., *A New Generation of $Ca^{2+}$ Indicators with Greatly Improved Fluorescence Properties*, Journal of Biological Chemistry, vol. 260, No. 6., 1985, pp. 3440-3450.
R. Y. Tsien, et al., *Calcium Homeostasis in Intact Lymphocytes: Cytoplasmic Free Calcium Monitored With a New, Intracellularly Trapped Fluorescent Indicator*, Journal of Cell Biology, vol. 94, Aug. 1982, pp. 325-334.

(Continued)

*Primary Examiner*—Shailendra Kumar
(74) *Attorney, Agent, or Firm*—Christie, Parker & Hale LLP

(57) ABSTRACT

A two-photon probe for real-time monitoring of intracellular magnesium ions is provided. Specifically, the two-photon probe is represented by Formula 1:

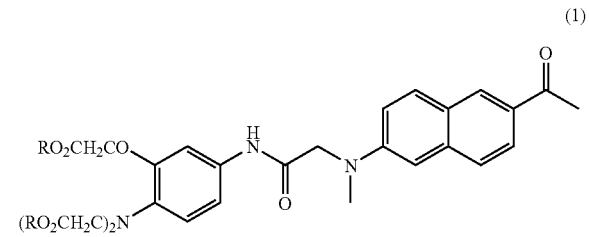

(1)

wherein R is H or $CH_2OCOCH_3$.

The two-photon probe is very suitable for real-time imaging of intracellular magnesium ions. The two-photon probe shows 17-fold two-photon excited fluorescence enhancement in response to $Mg^{2+}$, which is 7-fold stronger than commercial probes, thus enabling staining of cells in a greatly reduced amount. In addition, the two-photon probe has a sufficiently low molecular weight to stain cells and is very suitable for monitoring $Mg^{2+}$ ions present in the deep tissue. Furthermore, the two-photon probe can be effectively used for the quantitative as well as qualitative detection of intracellular magnesium ions. Further provided are a method for preparing the two-photon probe and a method for real-time monitoring of intracellular magnesium ions using the two-photon probe.

8 Claims, 13 Drawing Sheets
(6 of 13 Drawing Sheet(s) Filed in Color)

OTHER PUBLICATIONS

R. Y. Tsien, *Measurement of Cytosolic Free $Ca^{2+}$ with Quin2*, Methods in Enzymology, vol. 172, 1989, pp. 230-262.

A. Takahashi, et al., *Measurement of Intracellular Calcium*, Physiological Review, vol. 79, No. 4, Oct. 1999, pp. 1089-1125.

H. Szmacinski, et al., *Fluorescence Lifetime Characterization of Magnesium Probes: Improvement of Mg2+ Dynamic Range and Sensitivity Using Phase-Modulation Fluorometry*, Journal of Fluorescence, vol. 6, No. 2, 1996, pp. 83-95.

I. J. Reynolds, *Measurement of Cation Movement in Primary Cultures Using Fluorescent Dyes*, Current Protocols in Neuroscience, Supplement 4, 1998, pp. 7.11.1-7.11.17.

M. R. Cho, et al., *Transmembrane calcium influx induced by ac electric fields*, The FASEB Journal, vol. 13, Apr. 1999, pp. 677-683.

Haugland, R.P., *The Handbook: A Guide to Fluorescent Probes and Labeling Technologies*, 10th Edition, Molecular Probes, (2005), Eugene, OR, 9 pages.

* cited by examiner

TWO-PHOTON PROBE FOR REAL-TIME MONITORING OF INTRACELLULAR MAGNESIUM IONS, METHOD FOR PREPARING THE TWO-PHOTON PROBE AND METHOD FOR REAL-TIME MONITORING OF INTRACELLULAR MAGNESIUM IONS USING THE TWO-PHOTON PROBE

CROSS-REFERENCE TO RELATED APPLICATION

This application claims priority of Korean Patent Application Number 10-2007-0051131, filed on May 25, 2007.

BACKGROUND OF THE INVENTION

1. Field of the Invention

The present invention relates to a two-photon probe for real-time monitoring of intracellular magnesium ions, a method for preparing the two-photon probe, and a method for real-time monitoring of intracellular magnesium ions using the two-photon probe. More specifically, the present invention relates to a two-photon probe that has a sufficiently low molecular weight to stain cells and is suitable for real-time imaging of intracellular magnesium ions due to its very high two-photon fluorescence efficiency, a method for preparing the two-photon probe, and a method for real-time monitoring of intracellular magnesium ions using the two-photon probe.

2. Description of the Related Art $Mg^{2+}$ is one of the most abundant divalent metal ions in cells, and it plays crucial roles in many cellular processes such as proliferation and cell death as well as participating in the regulation of hundreds of enzymatic reactions. To detect intracellular $Mg^{2+}$, a variety of membrane-permeable fluorescent probes have been developed with some of them being commercially available (*The Handbooks*—A Guide to Fluorescent Probes and Labeling Technologies, 10th ed.; Haugland, R. P. Ed.; Molecular Probes: Eugene, Oreg., 2005.; H. Komatsu, N. Iwasawa, D. Citterio, Y. Suzuki, T. Kubota, K. Tokuno, Y. Kitamura, K. Oka, K. Suzuki, *J. Am. Chem. Soc.* 2004, 126, 16353-16360.; G. Farruggia, S. Iotti, L. Prodi, M. Montalti, N. Zaccheroni, P. B. Savage, V. Trapani, P. Sale, F. I. Wolf, *J. Am. Chem. Soc.* 2006, 128, 344-350.). Most of them are used as their acetoxymethyl (AM) esters, which can readily undergo enzymatic hydrolysis to regenerate the metal-ion probe inside the cell. However, confocal microscopy with one-photon (OP) fluorescent probes is limited for use near the tissue surface (<100 μm).

To observe cellular events deep inside the tissue, it is crucial to use two-photon microscopy (TPM). TPM employing two near-infrared photons for excitation offers a number of advantages over one-photon microscopy, including increased penetration depth (>500 μm), lower tissue autofluorescence and self-absorption, as well as reduced photodamage and photobleaching (W. R. Zipfel, R. M. Williams, W. W. Webb, *Nat. Biotechnol.* 2003, 21, 1369-1377; F. Helmchen, W. Denk, *Nat. Methods,* 2005, 2, 932-940.).

The extra penetration that TPM affords is of particular interest in tissue imaging because surface preparation artifacts such as damaged cells extends over 70 μm into the brain slice interior (R. M. Williams, W. R. Zipfel, W. W. Webb, *Curr. Opin. Chem. Biol.* 2001, 5, 603-608.). However, most of the OP fluorescent probes presently used for TPM have small two-photon action cross sections (φδ) that limit their use in TPM. Another limitation associated with tissue imaging is a mistargeting problem, which results from membrane-bound probes (*The Handbooks*—A Guide to Fluorescent Probes and Labeling Technologies, 10th ed.; Haugland, R. P. Ed.; Molecular Probes: Eugene, Oreg., 2005.; J. R. Long, R. S. Drago, *J. Chem. Ed.* 1982, 59, 1037-1039; K. J. Hirose, *Incl. Phenom. Macrocycl. Chem.* 2001, 39, 193-209.). As the probes can be accumulated in any membrane-enclosed structure within the cell and as the fluorescence quantum yield should be higher in the membrane than in the cytosol, it is practically difficult for the signals from membrane-bound probes to be separated from those of the probe-$Mg^{2+}$ complex.

Therefore, there is a need to develop efficient two-photon probes with 1) enhanced φδ values for brighter TPM images and 2) larger spectral shifts in different environments for better discrimination between the cytosolic and membrane-bound probes.

SUMMARY OF THE INVENTION

Thus, it is a first object of the present invention to provide a two-photon probe that is highly selective for various metals ions, particularly magnesium ions, present in living cells and live tissues and is suitable for real-time imaging of intracellular magnesium ions due to its very high two-photon fluorescence efficiency.

It is a second object of the present invention to provide a method for preparing the two-photon probe.

It is a third object of the present invention to provide a method for real-time monitoring of intracellular magnesium ions using the two-photon probe.

In order to accomplish the first object of the present invention, there is provided a two-photon probe for real-time monitoring of intracellular magnesium ions, represented by Formula 1:

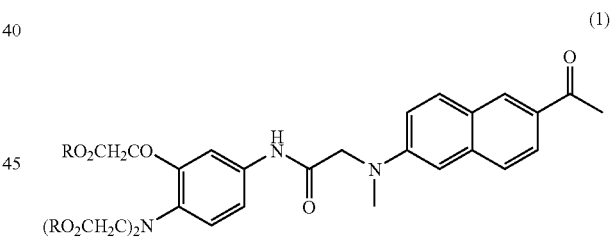

(1)

wherein R is H or $CH_2OCOCH_3$.

In order to accomplish the second object of the present invention, there is provided a method for preparing a two-photon probe for real-time monitoring of intracellular magnesium ions, represented by Formula 1:

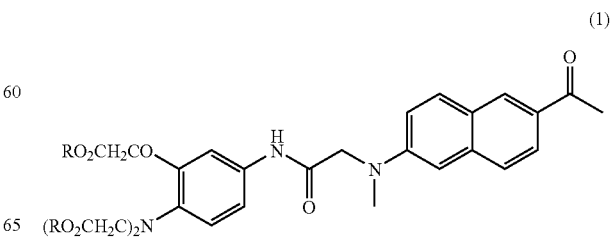

(1)

wherein R is H or CH$_2$OCOCH$_3$, the method comprising reacting 1-ethyl-3-(3-dimethylaminopropyl)carbodiimide hydrochloride, 4-dimethylaminopyridine and the compounds of Formulae 2 and 3:

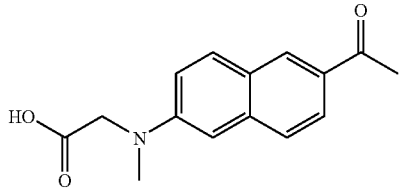

(2)

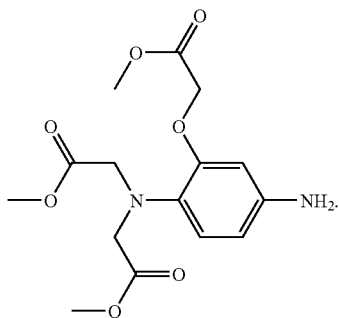

(3)

In an embodiment of the present invention, the compound of Formula 2 may be prepared by reacting methyl bromoacetate, Na$_2$HPO$_4$, NaI and the compound of Formula 4:

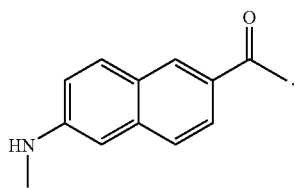

(4)

In a further embodiment of the present invention, the compound of Formula 4 may be prepared by reacting CH$_3$NH$_2$·HCl, Na$_2$S$_2$O$_3$, NaOH, H$_2$O and the compound of Formula 5:

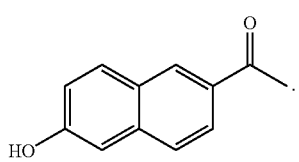

(5)

In another embodiment of the present invention, the compound of Formula 5 may be prepared by reacting HBr with the compound of Formula 6:

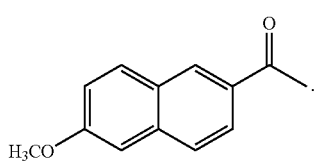

(6)

In order to accomplish the third object of the present invention, there is provided a method for real-time monitoring of intracellular magnesium ions, the method comprising introducing the two-photon probe into cells and imaging two-photon excited fluorescence emitted from the two-photon probe.

In an embodiment of the present invention, the two-photon excited fluorescence images may be obtained in the wavelength range of 500 to 620 nm.

In a further embodiment of the present invention, the intracellular magnesium ion concentration may be quantitatively determined by Equation 1:

$$[Mg^{2+}] = K_d[(F-F_{min})/(F_{max}-F)] \quad (1)$$

where $K_d$ is the dissociation constant of the two-photon probe for Mg$^{2+}$, F is the observed two-photon fluorescence intensity, $F_{min}$ is the minimum fluorescence intensity, and $F_{max}$ is the maximum fluorescence intensity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10a shows a brightfield image at 10× magnification, FIG. 10b is a two-photon microscopy (TPM) image with the same magnification, FIG. 10c is a TPM image at 40× magnification, and FIG. 10d is a TPM image at 100× magnification.

DESCRIPTION OF THE PREFERRED EMBODIMENTS

Figure 1A:
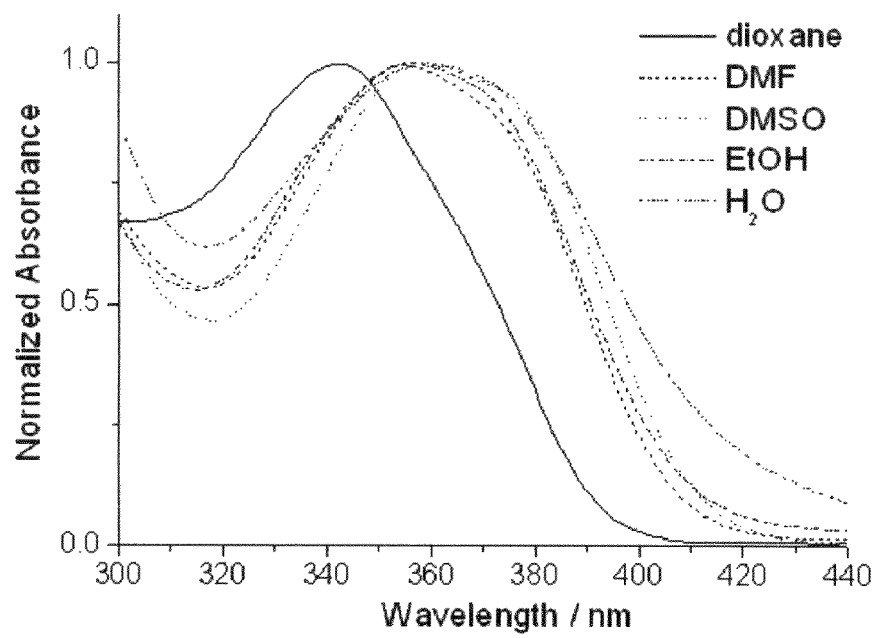
FIGS. 1a and 1b depict one-photon absorption (1a) and emission (1b) spectra of a two-photon probe according to the present invention.

The present invention will now be described in greater detail with reference to the accompanying drawings and exemplary embodiments.

The present invention provides a two-photon probe that can stain cells in a greatly reduced amount due to its very high two-photon fluorescence efficiency and has a sufficiently low molecular weight to stain cells, thus being suitable for real-time imaging of intracellular magnesium ions.

Specifically, the present invention provides a two-photon probe for real-time monitoring of intracellular magnesium ions, represented by Formula 1:

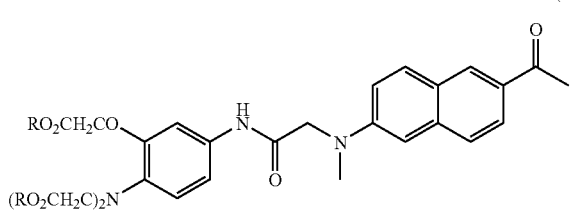

(1)

wherein R is H or $CH_2OCOCH_3$.

In Formula 1, the 2-acetyl-6-(dimethylamino)naphthalene moiety functions as a two-photon chromophore and the o-aminophenol-N,N,O-triacetic acid moiety functions as a $Mg^{2+}$ selective binding site. The two-photon probe of the present invention emits strong two-photon excited fluorescence (TPEF) on forming a complex with $Mg^{2+}$. Moreover, since the complex emits TPEF in a widely different wavelength range depending on the polarity of the environment, the TPEF due to the membrane-bound probes can be excluded from that of the complex by using different detection windows.

In the compound of Formula 1, R may be H or $CH_2OCOCH_3$. To enhance the cell permeability of the two-photon probe according to the present invention, the carboxylic acid moieties can be converted to esters ($CH_2OCOCH_3$).

The present invention also provides a method for preparing a two-photon probe for real-time monitoring of intracellular magnesium ions, represented by Formula 1:

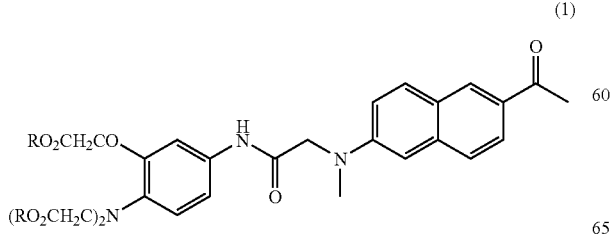

(1)

wherein R is H or $CH_2OCOCH_3$, the method comprising reacting 1-ethyl-3-(3-dimethylaminopropyl)carbodiimide hydrochloride, 4-dimethylaminopyridine and the compounds of Formulae 2 and 3:

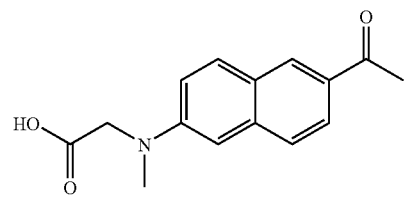

(2)

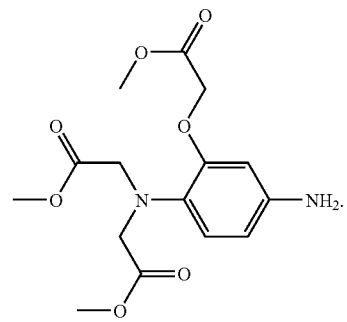

(3)

Preferably, the compound of Formula 2 is prepared by reacting methyl bromoacetate, $Na_2HPO_4$, NaI and the compound of Formula 4:

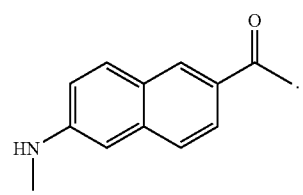

(4)

Preferably, the compound of Formula 4 is prepared by reacting $CH_3NH_2 \cdot HCl$, $Na_2S_2O_3$, NaOH, $H_2O$ and the compound of Formula 5:

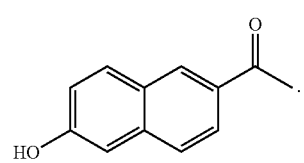

(5)

Preferably, the compound of Formula 5 is prepared by reacting HBr with the compound of Formula 6:

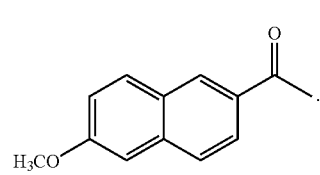

(6)

For reference, Reaction Scheme 1 shows exemplary reactions for the preparation of the compound of Formula 1 starting from the compound of Formula 6 compound.

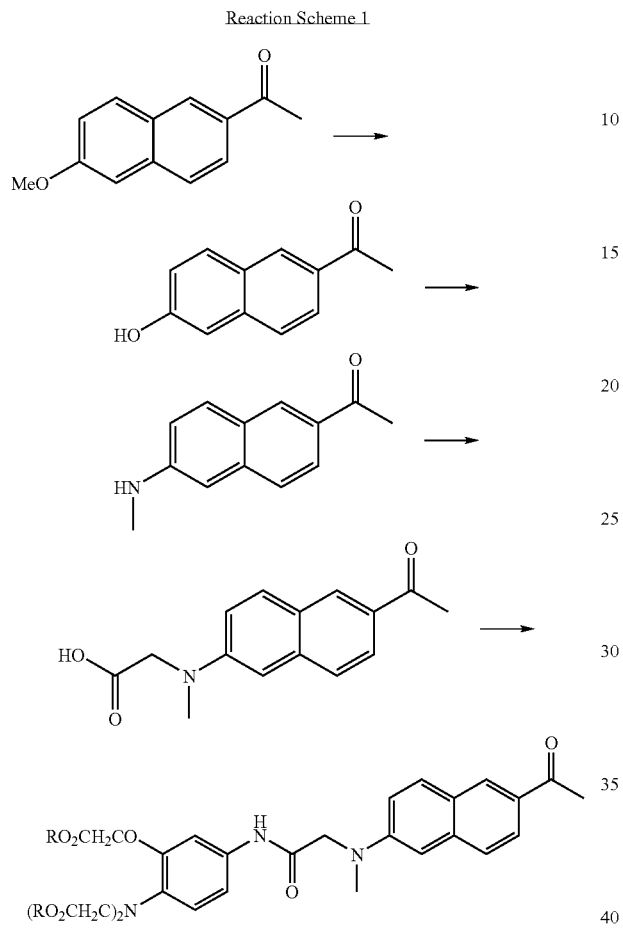

Reaction Scheme 1

As mentioned above, the hydrogen atoms of the carboxylic acid moieties may be replaced by $CH_2OCOCH_3$ to enhance the cell permeability of the two-photon probe according to the present invention. Preferably, this replacement is conducted by reacting bromoethyl acetate and triethylamine with the compound of Formula 1 (R=H).

The present invention also provides a method for real-time monitoring of intracellular magnesium ions, the method comprising introducing the two-photon probe into cells and imaging two-photon excited fluorescence emitted from the two-photon probe.

Particularly, in the case where the two-photon excited fluorescence images are obtained in the wavelength range of 500 to 620 nm, intracellular free $Mg^{2+}$ only can be selectively detected with minimum contribution from the membrane-bound two-photon probes, as will be described below.

Unlike the prior art methods, according to the real-time monitoring method of the present invention, the intracellular magnesium ions can be quantitatively detected as well as qualitatively analyzed. Preferably, the intracellular $Mg^{2+}$ ion concentration is determined by Equation 1:

$$[Mg^{2+}] = K_d[(F-F_{min})/(F_{max}-F)] \tag{1}$$

where $K_d$ is the dissociation constant of the two-photon probe according to the present invention for $Mg^{2+}$, F is the observed two-photon fluorescence intensity, $F_{min}$ is the minimum fluorescence intensity, and $F_{max}$ is the maximum fluorescence intensity.

Hereinafter, the present invention will be explained in more detail with reference to the following examples. However, these examples serve to provide further appreciation of the invention but are not meant in any way to restrict the scope of the invention.

EXAMPLES

Preparative Example 1

Preparation of the Two-Photon Probe of the Present Invention

In this example, the compound of Formula 7 was prepared.

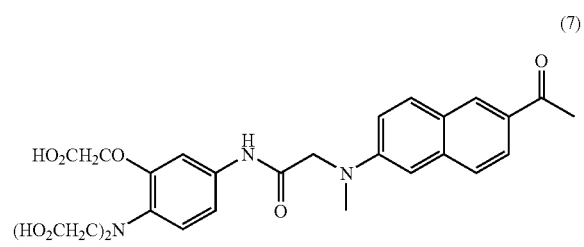

(7)

Preparative Example 1.1

6-acetyl-2-hydroxynaphthalene (Formula 8)

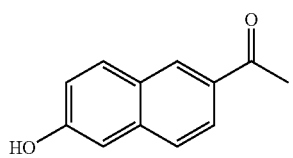

(8)

To a solution containing 6-acetyl-2-methoxynaphthalene (10.4 g, 52 mmol) in glacial acetic acid (100 mL), 48% HBr (43.0 g, 0.53 mol) was added. The mixture was stirred at 100° C. for 12 hr. Excess acetic acid was removed in vacuo, and the residue was taken up in ethyl acetate and washed with dilute $NaHCO_3$ and brine. The organic layer was dried with $MgSO_4$ and the solvent was removed in vacuo. The product was purified by column chromatography using ethyl acetate/hexane (1:1) as the eluent.

Yield 7.2 g (74%); m.p. 173° C.; IR (KBr): 3,362, 1,664 cm$^{-1}$; $^1$H NMR (300 MHz, CDCl$_3$): δ 8.41 (d, 1H, J=2 Hz), 7.99 (dd, 1H, J=9, J=2 Hz), 7.87 (d, 1H, J=9 Hz), 7.70 (d, 1H, J=9 Hz), 7.20 (d, 1H, J=2 Hz), 7.18 (dd, 1H, J=9, J=2 Hz), 5.70 (br s, 1H), 2.71 (s, 3H). Anal. Calcd. for $C_{12}H_{10}O_2$: C, 77.40; H, 5.41. Found: C, 77.52; H, 5.46.

Preparative Example 1.2

Preparation of 6-acetyl-N-methyl-2-naphthylamine (Formula 9)

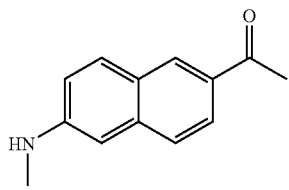

(9)

MeNH$_2$.HCl (14.2 g, 0.17 mol) was added to a mixture of the compound of Formula 8 (6.5 g, 35 mmol), Na$_2$S$_2$O$_5$ (13.3 g, 70 mmol), NaOH (7.0 g, 0.17 mol), and H$_2$O (200 mL) in a steel-bomb reactor and the mixture was stirred at 140° C. for 48 h. The product was collected by filtration, washed with water, and purified by flash column chromatography using chloroform/ethyl acetate (50:1) as the eluent. It was further purified by recrystallization from MeOH.

Yield 5.9 g (85%); m.p. 181° C.; IR (KBr): 3,347, 1,663 cm$^{-1}$; $^1$H NMR (300 MHz, CDCl$_3$): δ 8.30 (d, 1H, J=2 Hz), 7.93 (dd, 1H, J=9, J=2 Hz), 7.72 (d, 1H, J=9 Hz), 7.63 (d, 1H, J=9 Hz), 6.91 (dd, 1H, J=9, J=2 Hz), 6.77 (d, 1H, J=2 Hz), 4.17 (br s, 1H), 2.97 (s, 3H), 2.67 (s, 3H). Anal. Calcd. for $C_{13}H_{13}NO$: C, 78.36; H, 6.58; N, 7.03. Found: C, 78.32; H, 6.56; N, 7.08.

Preparative Example 1.3

Preparation of 6-acetyl-2-[N-methyl-N-(carboxy)amino]naphthalene (Formula 10)

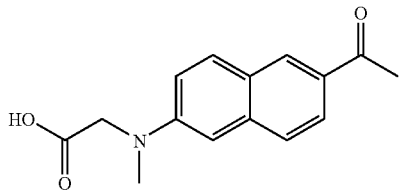

(10)

A mixture of the compound (4.5 g, 23 mmol) prepared in Preparative Example 1.2, methyl bromoacetate (5.2 g, 34 mmol), Na$_2$HPO$_4$ (4.8 g, 34 mmol) and NaI (1.4 g, 9.2 mmol) in MeCN (150 mL) was refluxed under N$_2$ for 18 h. The product was extracted with ethyl acetate, washed with brine, and purified by flash column chromatography using chloroform/ethyl acetate (30:1) as the eluent.

Yield 5.2 g (83%); m.p. 92° C.; IR (KBr): 1,754, 1,671 cm$^{-1}$; $^1$H NMR (300 MHz, CDCl$_3$): δ 8.32 (d, 1H, J=2 Hz), 7.92 (dd, 1H, J=9, J=2 Hz), 7.80 (d, 1H, J=9 Hz), 7.64 (d, 1H, J=9 Hz), 7.08 (dd, 1H, J=9, J=2 Hz), 6.88 (d, 1H, J=2 Hz), 4.23 (s, 2H), 3.74 (s, 3H), 3.21 (s, 3H), 2.67 (s, 3H). Anal. Calcd. for $C_{16}H_{17}NO_3$: C, 70.83; H, 6.32; N, 5.16. Found: C, 70.88 H; 6.35; N, 5.10.

A mixture of this intermediate (2.0 g, 7.4 mmol) and KOH (0.8 g, 14 mmol) in EtOH/H$_2$O (50/10 mL) was stirred for 5 h. The resultant solution was diluted with ice-water (100 mL) and concentrated HCl (aq) was added slowly at <5° C. until pH=3. The resulting precipitate was collected, washed with distilled water and purified by crystallization from MeOH.

Yield 1.6 g (84%); m.p. 158° C.; IR (KBr): 2,906, 1,739, 1,678 cm$^{-1}$; $^1$H NMR (400 MHz, CD$_3$OD): δ 8.39 (d, 1H, J=2 Hz), 7.86 (dd, 1H, J=9, J=2 Hz), 7.84 (d, 1H, J=9 Hz), 7.64 (d, 1H, J=9 Hz), 7.18 (dd, 1H, J=9, J=2 Hz), 6.93 (d, 1H, J=2 Hz), 4.27 (s, 2H), 3.19 (s, 3H), 2.65 (s, 3H); $^{13}$C NMR (100 MHz, CD$_3$OD): δ=199.3, 173.2, 149.8, 138.2, 130.9, 130.9, 130.8, 126.4, 125.7, 124.1, 116.0, 105.5, 53.5, 38.7, 25.4 ppm; Anal. Calcd. for $C_{15}H_{15}NO_3$: C, 70.02; H 5.88; N, 5.44. Found: C, 70.08; H, 5.79; N, 5.45.

Preparative Example 1.4

Preparation of the Two-Photon Probe of the Present Invention (Formula 7)

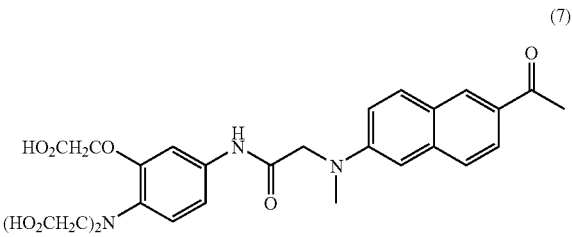

(7)

A mixture of the compound (0.50 g, 1.9 mmol) of Formula 10 prepared in Preparative Example 1.3 and 1-ethyl-3-(3-dimethylaminopropyl)carbodiimide hydrochloride (0.44 g, 2.3 mmol) in DMF (20 mL) was stirred for 20 min. To this mixture, the compound (0.71 g, 2.1 mmol) of Formula 12 and 4-dimethylaminopyridine (0.033 g, 0.29 mmol) were added and stirred for 12 h under N$_2$. The compound of Formula 11 was prepared by the literature methods (B. Metten, M. Smet, N. Boens, W. Dehaen, *Synthesis* 2005, 11, 1838).

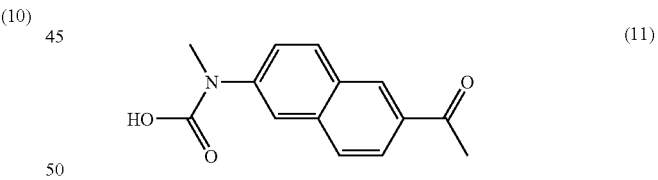

(11)

The product was extracted with ethyl acetate, dried over MgSO$_4$, and the solvent was removed in vacuo. The product was purified by column chromatography using chloroform/ethyl acetate (1:1) as the eluent. It was further purified by recrystallization from MeOH to obtain a white solid.

Yield 0.64 g (58%); m.p. 120° C.; IR (KBr): 3,264, 1,754, 1,663 cm$^{-1}$; $^1$H NMR (300 MHz, CDCl$_3$): δ 8.35 (d, 1H, J=2 Hz), 8.15 (s, 1H), 7.96 (dd, 1H, J=9, J=2 Hz), 7.86 (d, 1H, J=9 Hz), 7.69 (d, 1H, J=9 Hz), 7.35 (d, 1H, J=2 Hz), 7.12 (dd, 1H, J=9, J=2 Hz), 7.05 (d, 1H, J=2 Hz), 6.84 (d, 1H, J=9 Hz), 6.80 (dd, 1H, J=9, J=2 Hz), 4.68 (s, 2H), 4.16 (s, 4H), 4.09 (s, 2H), 3.77 (s, 3H), 3.69 (s, 6H), 3.22 (s, 3H), 2.68 (s, 3H); Anal. Calcd. for $C_{30}H_{33}N_3O_9$: C, 62.17; H, 5.74; N, 7.25. Found: C, 62.22; H, 5.76; N, 7.16.

This ester (0.5 g, 0.86 mmol) was hydrolyzed by the method described in Preparative Example 1.3. The resulting precipitate was collected, washed with distilled water, and purified by crystallization from MeOH—CHCl$_3$-petroleum ether. Yield 0.32 g (69%); m.p. 148° C.; IR (KBr): 3,271, 2,905, 1,747, 1,663 cm$^{-1}$; $^1$H NMR (400 MHz, CD$_3$OD): 8.38 (d, 1H, J=2 Hz), 7.84 (d, 1H, J=9 Hz), 7.83 (d, 1H, J=9 Hz), 7.63 (d, 1H, J=9 Hz), 7.22 (s, 1H), 7.18 (dd, 1H, J=9, J=2 Hz), 7.03 (dd, 1H, J=9, J=2 Hz), 6.97 (d, 1H, J=2 Hz), 6.85 (d, 1H, J=9.0 Hz), 4.61 (s, 2H), 4.22 (s, 2H), 4.06 (s, 4H), 3.20 (s, 3H), 2.62 (s, 3H); $^{13}$C NMR (100 MHz, CD$_3$OD):=199.2, 174.3, 171.1, 169.7, 150.2, 149.9, 138.0, 135.9, 133.3, 130.9, 130.8, 130.7, 126.3, 125.8, 124.0, 120.0, 116.2, 113.8, 107.1, 105.8, 65.3, 56.4, 54.3, 39.1, 25.2 ppm; Anal. Calcd. for C$_{27}$H$_{27}$N$_3$O$_9$: C, 60.33; H, 5.06; N, 7.82. Found: C, 60.31; H, 5.12; N, 7.78.

Preparative Example 1.5

Preparation of the Two-Photon Probe of the Present Invention (Formula 12)

Figure 1B:
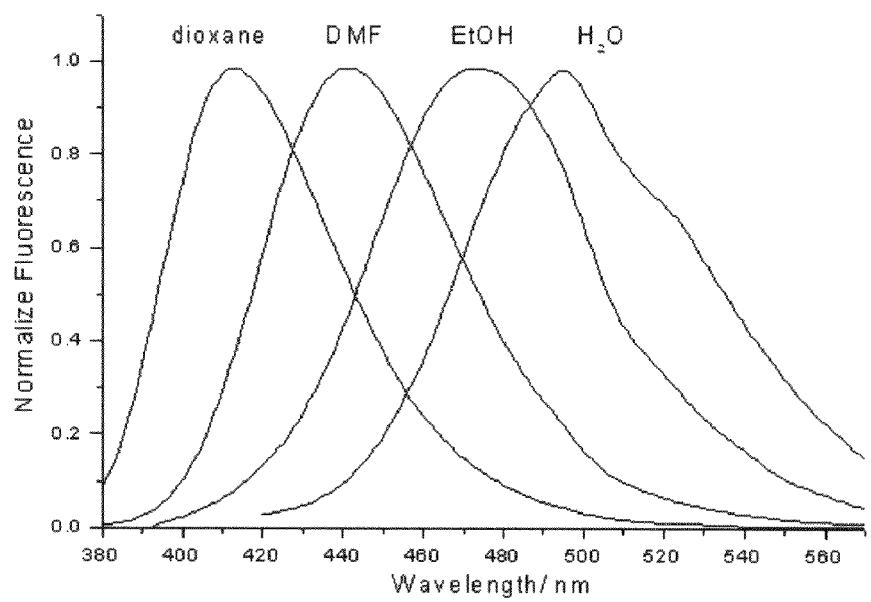

The one-photon absorption and emission spectra of the compound of Formula 13 are depicted in FIGS. 1a and 1b. The emission ($\lambda_{max}^{(1)}$) and fluorescence ($\lambda_{max}^{fl}$) maxima of the compound of Formula 13 in various solvents are shown in Table 1.

TABLE 1

| Compound | Solvent (E$_T^N$)* | $\lambda_{max}^{(1)}$ (nm) | $\lambda_{max}^{fl}$ (nm) |
| --- | --- | --- | --- |
| Formula 13 | 1,4-dioxane (0.164) | 344 | 413 |
|  | DMF (0.386) | 356 | 441 |
|  | Ethanol (0.654) | 359 | 473 |
|  | H$_2$O (1.000) | 363 | 495 |

*The numbers in the parenthesis are normalized empirical parameter of solvent polarity (C. Reichardt, Chem. Rev. 1994, 94, 2319-2358.).

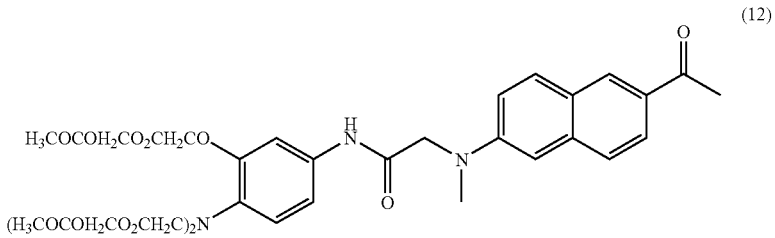

A mixture of the compound (0.15 g, 0.28 mmol) of Formula 11 prepared in Preparative Example 1.4, bromomethyl acetate (0.34 g, 2.2 mmol), and Et$_3$N (0.22 g, 1.7 mmol) in CHCl$_3$ (5 mL) was stirred under N$_2$ for 15 h. The solution was removed in vacuo and the crude product was purified by column chromatography using ethyl acetate/hexane (3:1) as the eluent. It was further purified by recrystallization from MeOH to obtain a white solid.

Yield 0.12 g (58%); m.p. 104° C.; IR (KBr): 3,257, 1,754, 1,708, 1,663 cm$^{-1}$; $^1$H NMR (400 MHz, CDCl$_3$): δ 8.35 (d, 1H, J=2 Hz), 8.18 (s, 1H), 7.97 (dd, 1H, J=9, J=2 Hz), 7.87 (d, 1H, J=9 Hz), 7.70 (d, 1H, J=9 Hz), 7.34 (d, 1H, J=2 Hz), 7.15 (dd, 1H, J=9, J=2 Hz), 7.05 (d, 1H, J=2 Hz), 6.89 (dd, 1H, J=9, J=2 Hz), 6.84 (d, 1H, J=9 Hz), 5.80 (s, 2H), 5.75 (s, 4H), 4.71 (s, 2H), 4.18 (s, 4H), 4.09 (s, 2H), 3.23 (s, 3H), 2.66 (s, 3H), 2.09 (s, 6H), 2.07 (s, 3H); $^{13}$C NMR (100 MHz, CDCl$_3$):=δ 197.9, 170.1, 169.7, 169.7, 168.0, 167.7, 150.1, 149.2, 137.3, 135.9, 133.0, 132.4, 131.6, 130.3, 127.0, 126.7, 125.3, 121.0, 116.7, 114.1, 107.8, 107.7, 79.5, 77.4, 65.9, 59.6, 53.7, 40.4, 26.7, 20.9, 20.8 ppm; Anal. Calcd. for C$_{36}$H$_{39}$N$_3$O$_5$: C, 57.37; H, 5.22; N, 5.58. Found: C, 57.32; H, 5.31; N, 5.52.

Example 1

Absorption Spectroscopic Measurements

Absorption spectra were recorded on a Hewlett-Packard 8453 diode array spectrophotometer, and fluorescence spectra were obtained with Amico-Bowman series 2 luminescence spectrometer with a 1 cm standard quartz cell. The fluorescence quantum yield was determined by using Coumarin 307 as the reference by the literature method (J. N. Demas, G. A. Crosby, J. Phys. Chem. 1971, 75, 991.).

FIGS. 1a and 1b and Table 1 show that a large bathochromic shift was observed with increasing solvent polarity, indicating the utility of the compound of Formula 13 as a polarity probe.

Example 2

Measurements of Absorbance Change with Varying Mg$^{2+}$ Concentrations

Figure 2A:
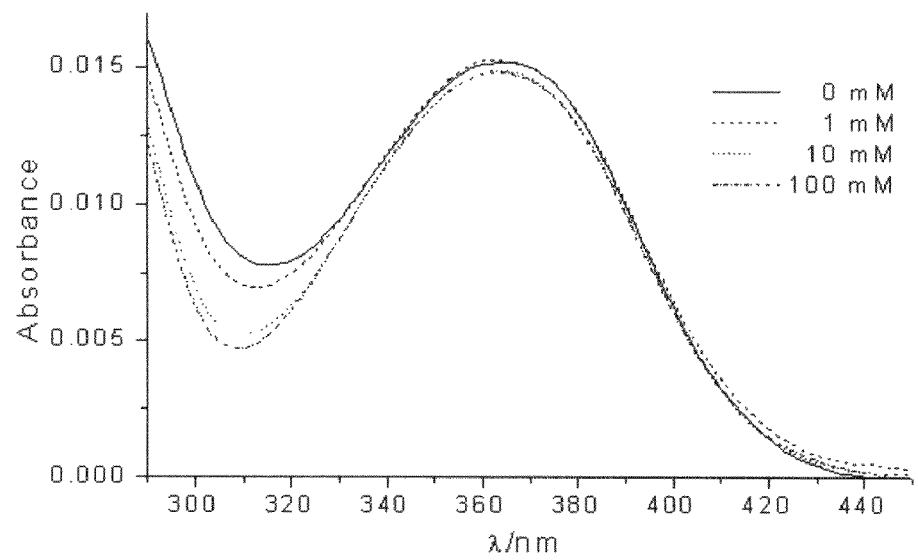
FIGS. 2a, 2b and 2c show one-photon absorption (2a), one-photon emission (2b) and two-photon fluorescence (2c) spectra of a two-photon probe according to the present invention in the presence of various concentrations of Mg$^{2+}$.
Figure 2B:
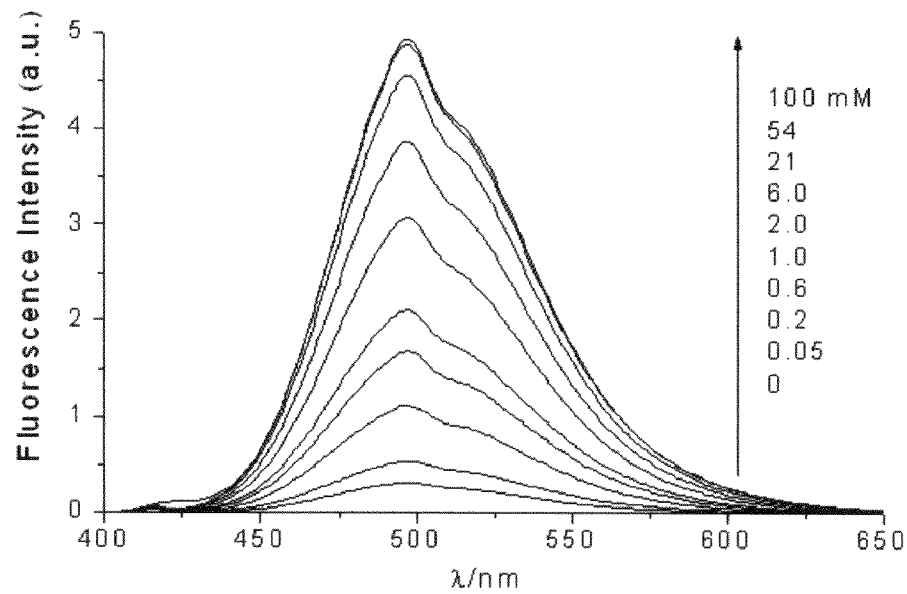

FIGS. 2a and 2b show the spectral response of the compound of Formula 7 toward Mg$^{2+}$. When Mg$^{2+}$ was added to the compound of Formula 7 in Tris buffer solution (10 mM, pH 7.05), there was a slight change in the absorption spectrum (FIG. 2b). In contrast, a dramatic increase in the fluorescence was observed with increasing Mg$^{2+}$ concentrations probably as a result of the blocking of the photo-induced electron-transfer (PET) process by metal ion complexation (FIG. 2b). The fluorescence enhancement factor was observed to be 17 in the presence of 100 mM Mg$^{2+}$.

Figure 2C:
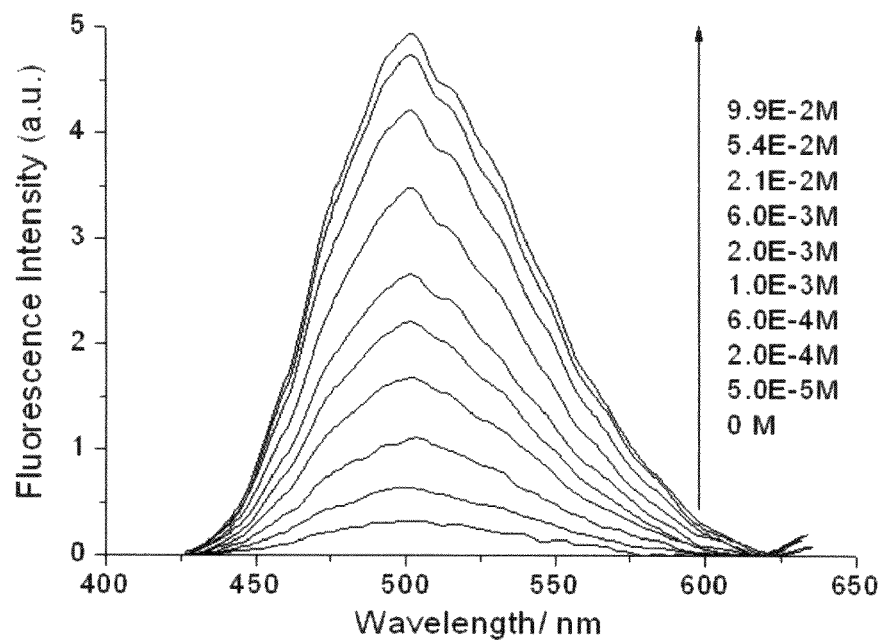
Figure 3A:
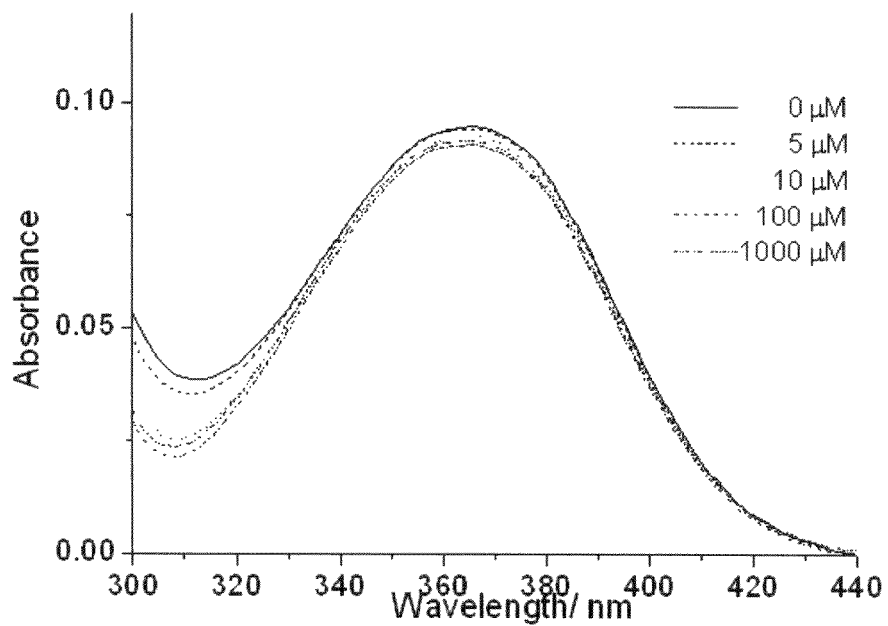
FIGS. 3a, 3b and 3c show one-photon absorption (3a), one-photon emission (3b) and two-photon fluorescence (3c) spectra of a two-photon probe according to the present invention in the presence of various concentrations of Ca$^{2+}$.
Figure 3B:
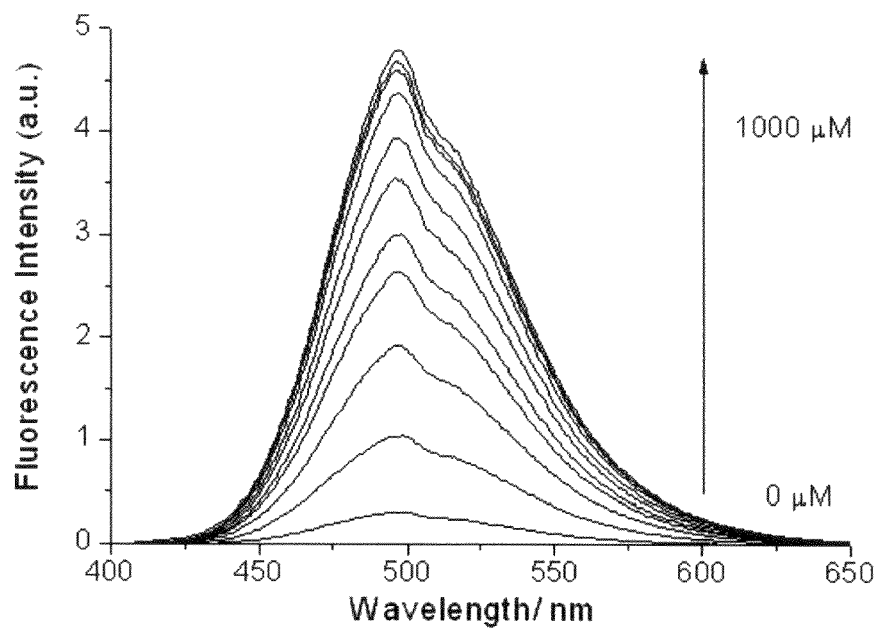
Figure 3C:
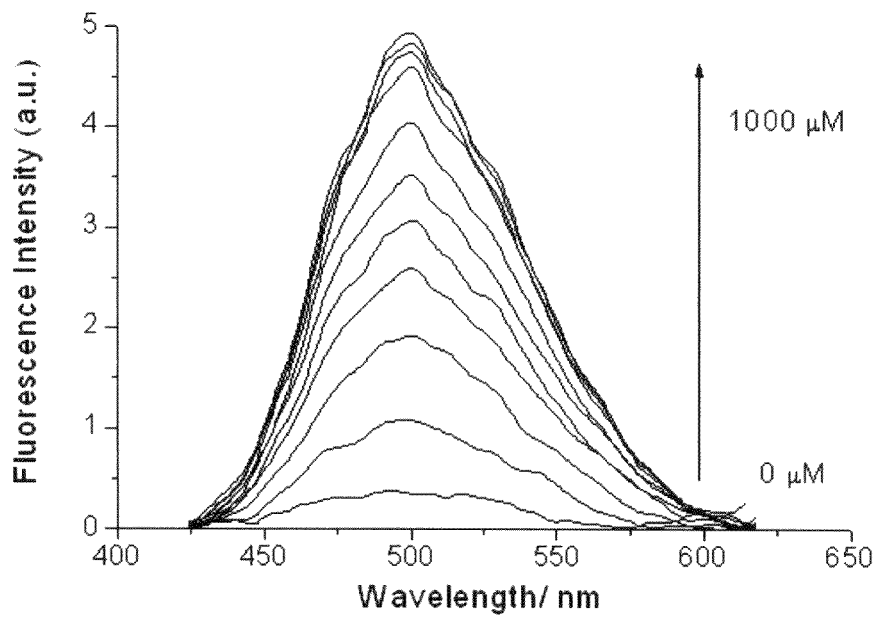

A nearly identical result was observed in the two-photon process, and FIG. 2c shows two-photon fluorescence spectra in the presence of various concentrations of MgCl$_2$ (0-100 mM). Furthermore, FIGS. 3a, 3b and 3c show one-photon absorption (3a), one-photon emission (3b), and two-photon fluorescence (3c) spectra of the compound of Formula 7 in the presence of Ca$^{2+}$ (0-1,000 μM).

Example 3

Benesi-Hildebrand Plot

The complexation modes of the compound of Formula 7 for Mg$^{2+}$ and Ca$^{2+}$ were determined from a Benesi-Hildebrand plot analysis (H. A. Benesi, J. H. Hildebrand, *J. Am. Chem. Soc.* 1949, 71, 2703.). Based on the assumption that the fluorescence change is only induced by the formation of a 1:1 complex between the compound (L) of Formula 7 and metal ions (M), the total probe concentration and the fluorescence intensity are defined as $[L]_0=[L]+[LM]$ and $F=\phi_L[L]+\phi_{ML}[ML]$, respectively, where $[L]_0$ and $[M]_0$ are the total concentration, [L] and [LM] are the equilibrium concentration of L and M, respectively, and $\phi_L$ and $\phi_{ML}$ are the fluorescence quantum yields for free and complexed forms of the compound of Formula 7. If $[M]_0 \gg [L]_0$, the Benesi-Hildebrand type equation can be derived as, $$\frac{1}{F - F_{min}} = \frac{1}{(\phi_{ML} - \phi_L)[L]_0} + \frac{1}{K[L]_0(\phi_{ML} - \phi_L)[M]_0}. \quad (2)$$

Figure 4A:
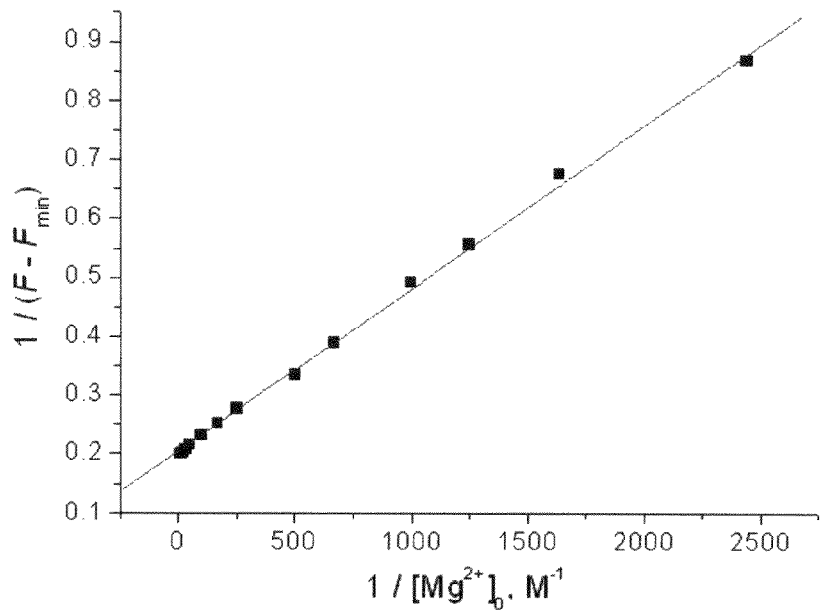
FIGS. 4a and 4b show the plots of 1/(F−F$_{min}$) vs 1/[Mg$^{2+}$] for the binding of a two-photon probe according to the present invention with Mg$^{2+}$ (4a) and Ca$^{2+}$ (4b).
Figure 4B:
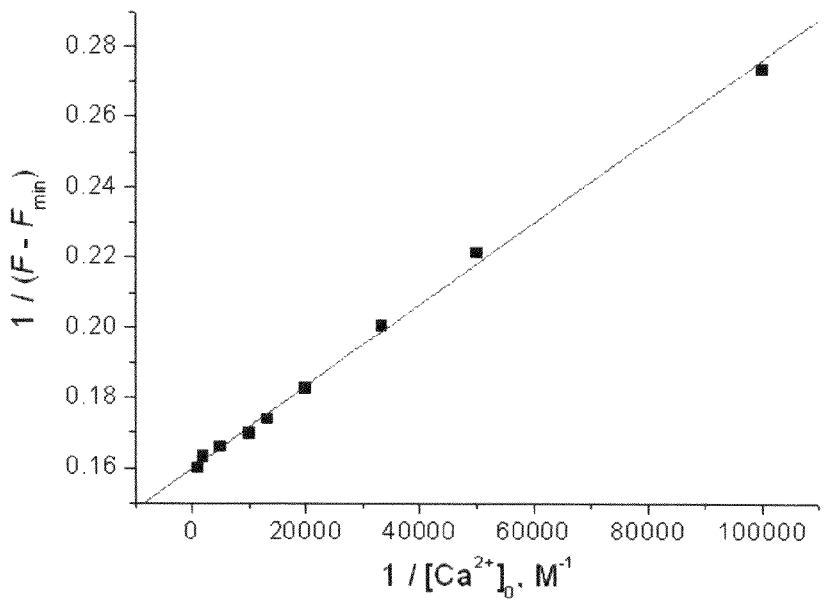

If a 1:1 metal-probe complex is formed between the compound of Formula 7 and metal ions, a Benesi-Hildebrand plot of the data according to Equation 2 should be linear (H. A. Benesi, J. H. Hildebrand, *J. Am. Chem. Soc.* 1949, 71, 2703.), FIGS. 4a and 4b show that the plots of $1/(F-F_{min})$ vs $1/[Mg^{2+}]$ for the binding of the compound of Formula 7 with $Mg^{2+}$ (4a) and $Ca^{2+}$ (4b). The plots are linear, confirming the 1:1 complexation.

Example 4

Determination of Dissociation Constants

The dissociation constant ($K_d$) for $Mg^{2+}$-EGTA at pH 7.05 in 100 mM KCl, 20 mM NaCl at 24° C. was calculated using the program WinMAXC (C. Patton, Stanford University, Palo Alto, Calif.). The value was estimated to be 28 mM. Free $[Mg^{2+}]$ level in the solution was controlled by $Mg^{2+}$-EGTA buffers using $K_d$=28 mM (G. Grynkiewicz, M. Poenie, R. Y. Tsien. *J. Biol. Chem.* 1985, 260, 3440.).

In order to determine the $K_d$ for $Mg^{2+}$-the compound (Formula 7) complex, the fluorescence spectrum was recorded with the compound (2 µM) of Formula 7 in 3.0 mL of 10 mM Tris, 100 mM KCl, 20 mM NaCl and 1 mM EGTA, adjusted with HCl to pH 7.05 at 24° C. Then 1.5 µL of this solution was discarded and replaced by 1.5 µL of a solution containing the compound (2 µM) of Formula 7, 103.6 mM $MgCl_2$, 4.6 mM EGTA and 10 mM Tris, pH 7.05, and the spectrum was recorded.

Since the former stock had 1 mM free EGTA but the latter had 100 mM free $Mg^{2+}$, the 99.95:0.05 (v/v) composite went to 0.05 mM free $Mg^{2+}$. Further iterations attained 0.1, 0.2, 0.4, 0.6, 0.8, 1.0, 1.5, 2.0, 4.0, 6.0, 10, 21, 32, and 54 mM free $Mg^{2+}$ by successively discarding 1.5, 3.0, 6.0, 6.0, 6.0, 6.5, 15, 15, 61, 63, 128, 365, 420, and 970 µl of the mixture and replacing each with an equal volume of the high-Mg stock solution.

The dissociation constant ($K_d$) for $Ca^{2+}$-EGTA at pH 7.2 in 100 mM KCl and 30 mM MOPS was calculated as described above. The value was estimated to be 144 nM. A series of calibration solutions containing various $[Ca^{2+}]$ was prepared by mixing two solutions (solution A containing 10 mM $K_2$EGTA and solution B containing 10 mM CaEGTA) in various ratios, except for 50-1000 mM concentrations which were obtained by addition of $CaCl_2$ (G. Grynkiewicz, M. Poenie, R. Y. Tsien. *J. Biol. Chem.* 1985, 260, 3440; R. Y. Tsien, T. Pozzan, T. J. Rink. *J. Cell Biol.* 1982, 94, 325; R. Y. Tsien, T. Pozzan, *Methods Enzymol.* 1989, 172, 230; A. Takahashi, P. Camacho, J. D. Lechleiter, B. Herman. *Physiol. Rev.* 1999, 79, 1089.). Both solutions contained 100 mM KCl, 30 mM MOPS, and they were adjusted to pH 7.2.

When a 1:1 metal-ligand complex is formed between the compound of Formula 7 and $Mg^{2+}$, the equilibrium can be described by Equation 3:

$$[LM]^2 - ([L]_0+[M]_0+K_d)[LM]+[L]_0[M]_0=0 \quad (3)$$

where L and M represent the compound of Formula 7 and $Mg^{2+}$, respectively.

Figure 5A:
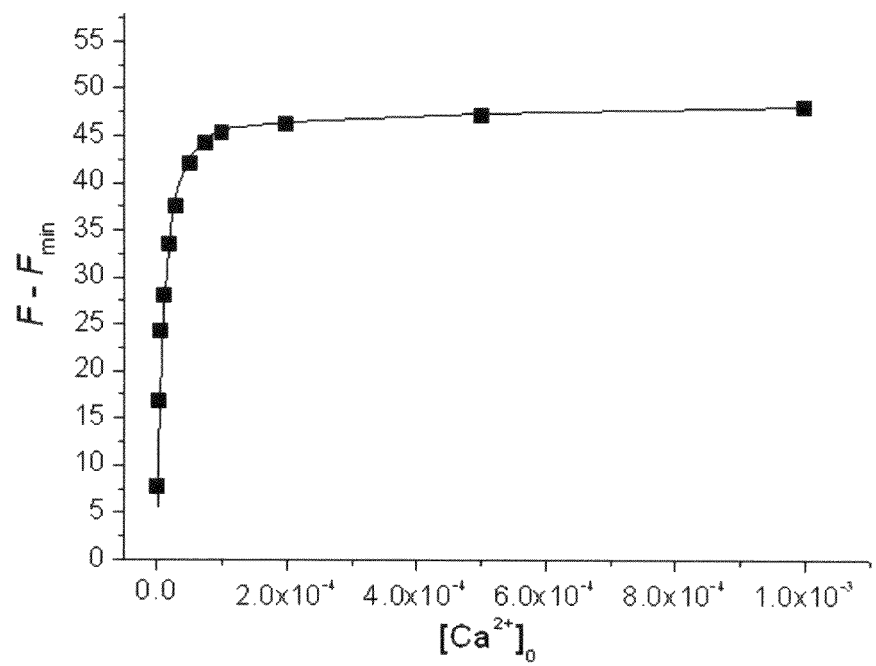
FIGS. 5a and 5b show a titration curve (5a) fitted to Equation 5 and a two-photon excited fluorescence titration curve (5b) in a method for real-time monitoring of intracellular magnesium ions according to the present invention.

The total probe and metal ion concentration are defined as $[L]_0=[L]+[LM]$ and $[M]_0=[M]+[LM]$, respectively. With $[L]_0$ and $[M]_0$, the value of $K_d$ is given by Equation 4 or 5:

$$[LM] = \frac{([L]_0 + [M]_0 + K_d) - \sqrt{([L]_0 + [M]_0 + K_d)^2 - 4[L]_0[M]_0}}{2}; \quad (4)$$

$$(F - F_{min}) = \left(\frac{([L]_0 + [M]_0 + K_d) - \sqrt{([L]_0 + [M]_0 + K_d)^2 - 4[L]_0[M]_0}}{2[L]_0}\right)(F_{max} - F_{min}) \quad (5)$$

where F is the observed fluorescence intensity, $F_{min}$ is the minimum fluorescence intensity, and $F_{max}$ is the maximum fluorescence intensity. The $K_d$ value that best fits the titration curve (FIG. 5a) with Equation 5 was calculated by using the Excel program as reported (J. R. Long, R. S. Drago, *J. Chem. Ed.* 1982, 59, 1037; K. Hirose, *J. Incl. Phenom. Macrocyc. Chem.* 2001, 39, 193).

Figure 5B:
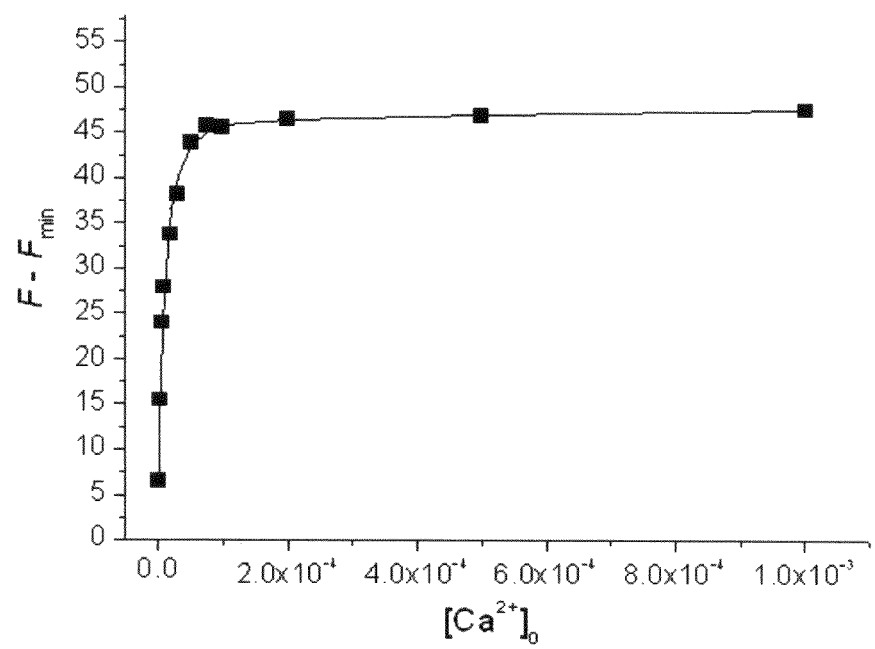

In order to determine the $K_d$ for the two-photon process, the TPEF spectra were obtained with a DM IRE2 Microscope (Leica) excited by a mode-locked titanium-sapphire laser source (Coherent Chameleon, 90 MHz, 200 fs) set at wavelength 780 nm and output power 1,230 mW, which corresponded to approximately 10 mW average power in the focal plane. The TPEF titration curves (FIG. 5b) were obtained and fitted to Equation 5.

Dissociation constants ($K_d$) for the one-photon processes were calculated from the fluorescence titration curves. The $K_d$ values for $Mg^{2+}$ and $Ca^{2+}$ were (1.4±0.1) mM and (9.0±0.3) mM, respectively, which were very similar to those measured for the two-photon processes [$K_d$=(1.6±0.1) mM ($Mg^{2+}$), (11±1) mM ($Ca^{2+}$)]. This result indicates the operation of a similar mechanism in both processes during the binding events.

Example 5

Measurements of Selectivity Toward Metal Ions

Figure 6A:
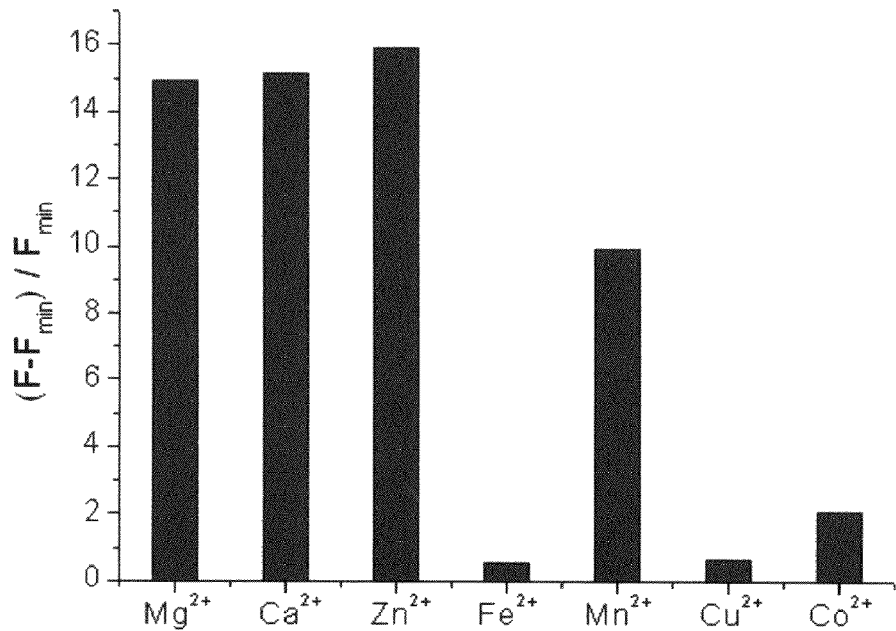
FIG. 6a shows the selectivity of a two-photon probe according to the present invention toward metal cations other than Mg$^{2+}$.

The selectivity toward other metal cations is shown in FIG. 6a. The compound of Formula 7 showed a modest to strong response toward $Mg^{2+}$, $Ca^{2+}$, $Zn^{2+}$, and $Mn^{2+}$, and a much weaker response toward $Fe^{2+}$, $Cu^{2+}$, and $Co^{2+}$ ions. The metal ion selectivity of the compound of Formula 7 is similar to those reported for MgG and Mag-Fura-2 (*The Handbooks*—A Guide to Fluorescent Probes and Labeling Technologies, 10th ed.; Haugland, R. P. Ed.; Molecular Probes: Eugene, Oreg., 2005.).

Figure 6B:
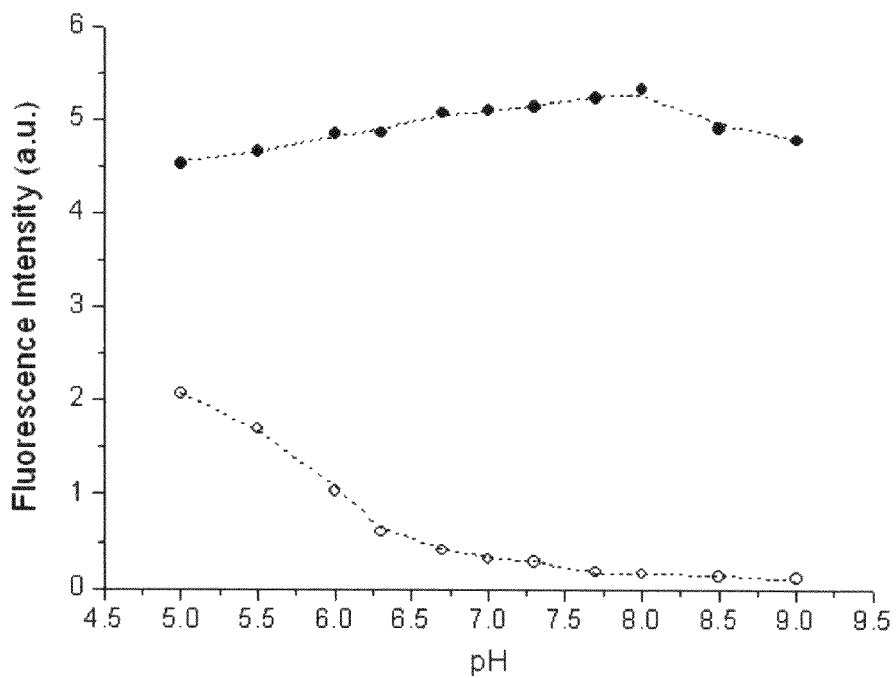
FIG. 6b shows the effect of pH on the fluorescence intensity of a two-photon probe according to the present invention.

Because the intracellular concentration of free $Mg^{2+}$ (0.1-6.0 mM) is much higher than that of $Ca^{2+}$ (10 nM-1 µM) and as chelatable $Zn^{2+}$ is essentially nonexistent except in specialized areas, the compound of Formula 7 can detect $Mg^{2+}$ without interference from $Ca^{2+}$ and $Zn^{2+}$. Furthermore, the compound of Formula 7 and $Mg^{2+}$-the compound (Formula 7) are pH-insensitive in the biologically relevant pH range (FIG. 6b).

Example 6

Figure 7:
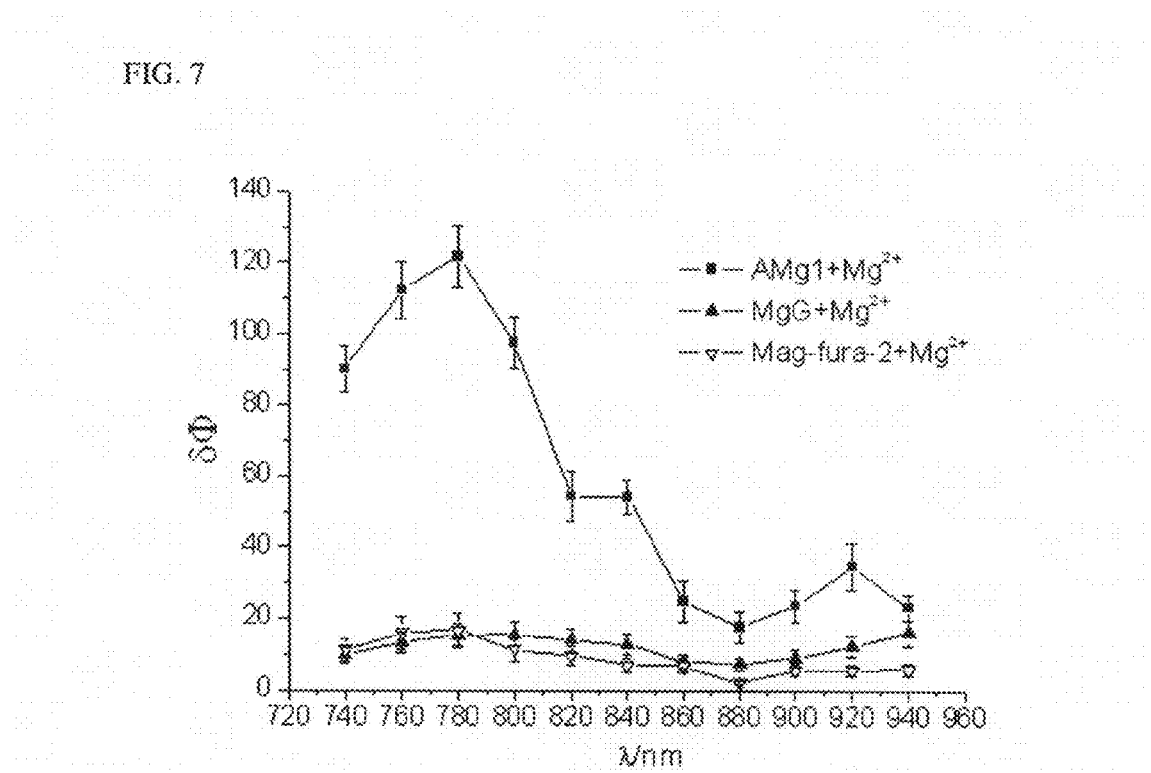
FIG. 7 is a graph comparing two-photon spectral characteristics of Mg$^{2+}$ complexes with a two-photon probe according to the present invention and prior art probes.

Comparison With Two-Photon Spectral Characteristics of Complexes of Commercial Probes The two-photon spectral characteristics of $Mg^{2+}$ complexes with the compound of Formula 7, MgG, and Mag-fura-2 in buffer solutions are depicted and compared in FIG. 7. The photophysical data for the magnesium ion probes are enumerated in Table 2.

TABLE 2

| Compound[1] | $\lambda_{max}^{(1)}$ (nm)[2] | $\lambda_{max}^{fl}$ (nm)[2] | $\lambda_{max}^{(2)}$ (nm)[3] | $\phi$[4] | $\delta_{max}$[5] | $\phi\delta$[6] |
|---|---|---|---|---|---|---|
| Formula 13 | 360 | 495 | ND[7] | 0.07[8] | ND[7] | ND[7] |
| Formula 7 | 365 | 498 | ND[7] | 0.04 | ND[7] | ND[7] |
| Formula 7-$Mg^{2+}$ | 365 | 498 | 780 | 0.58 | 215 | 125 |
| Mag-fura-2-$Mg^{2+}$ | 330[9] | 491[9] | 780 | 0.30[9] | 56 | 17 |
| MgG-$Mg^{2+}$ | 506[9] | 532[9] | 800 | 0.42[9] | 37 | 16 |

[1] All data were measured in 10 mM Tris buffer (100 mM KCl, 20 mM NaCl, 1 mM EGTA, pH 7.05) in the absence and presence (50 mM) of $MgCl_2 \cdot 6H_2O$.
[2] $\lambda_{max}$ of one-photon absorption and emission spectra.
[3] $\lambda_{max}$ of two-photon excitation spectra.
[4] Fluorescence quantum yield, ±10%.
[5] The peak two-photon cross section in $10^{-50}$ cm$^4$ s/photon (GM), ±15%.
[6] Two-photon action cross section.
[7] Not determined. The two-photon excited fluorescence intensity was too weak to measure the cross section accurately.
[8] $\phi = 0.32 \pm 0.02$ in DMF.
[9] H. Szmacinski, J. R. Lakowicz, J. Fluoresc. 1996, 6, 83-95.

This result indicates that TPM images would be much brighter when stained with the compound of Formula 7 than with the commercial probes.

Example 7

Imaging of Cells Using the Two-Photon Probes of the Present Invention

Hep3B cells were cultured in Dulbecco's modified Eagle's medium (DMEM) supplemented with penicillin/streptomycin and 10% fetal bovine serum(FBS) in a $CO_2$ incubator at 37° C. Hep3B cells were washed three times with serum-free media, and then incubated with the compound (2 µM) of Formula 13 in serum-free media for 30 min at 37° C. The cells were washed three times with serum-free media, and then imaged after further incubation in serum-free media for 15 min.

Two-photon fluorescence microscopy images of Hep3B cells labeled with the compound of Formula 13 were obtained with spectral confocal and multiphoton microscopes (Leica TCS SP2) with a ×100 oil objective and numerical aperture (NA)=1.30. The two-photon fluorescence microscopy images were obtained by exciting the probes with a mode-locked titanium-sapphire laser source (Coherent Chameleon, 90 MHz, 200 fs) set at wavelength 780 nm. To obtain images at 360-620 nm, 360-460 nm, and 500-620 nm range, internal PMTs were used to collect the signals in an 8 bit unsigned 512×512 pixels at 400 Hz scan speed.

Figure 8A:
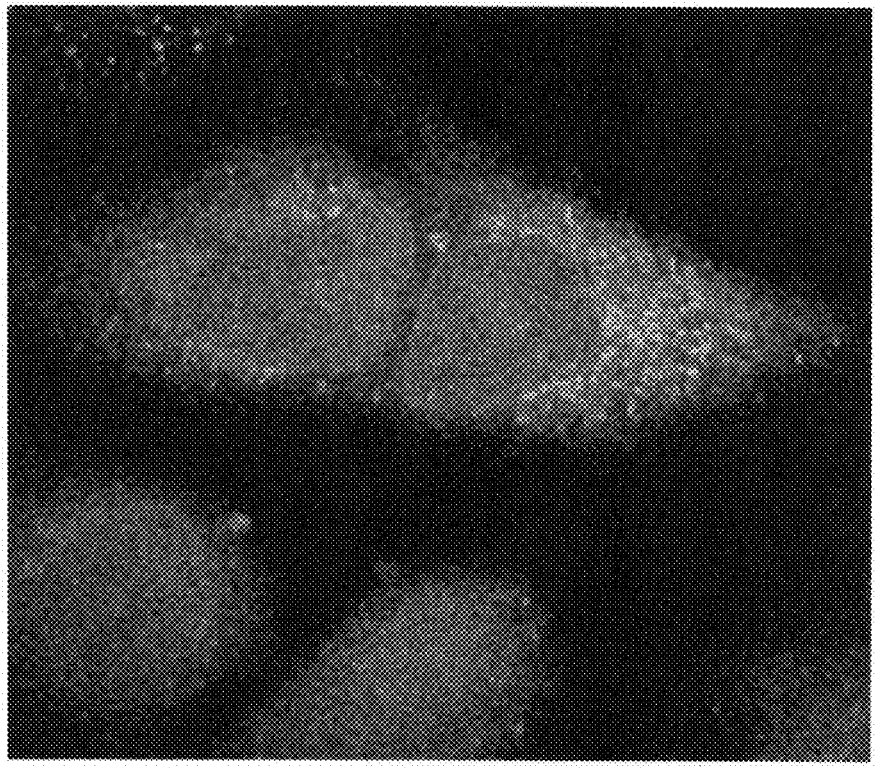
FIGS. 8a, 8b and 8c are two-photon microscopy (TPM) images collected at 360-620 nm (8a), 360-460 nm (8b) and 500-620 nm (8c) of Hep3B cells labeled with a two-photon probe of the present invention.
Figure 8B:
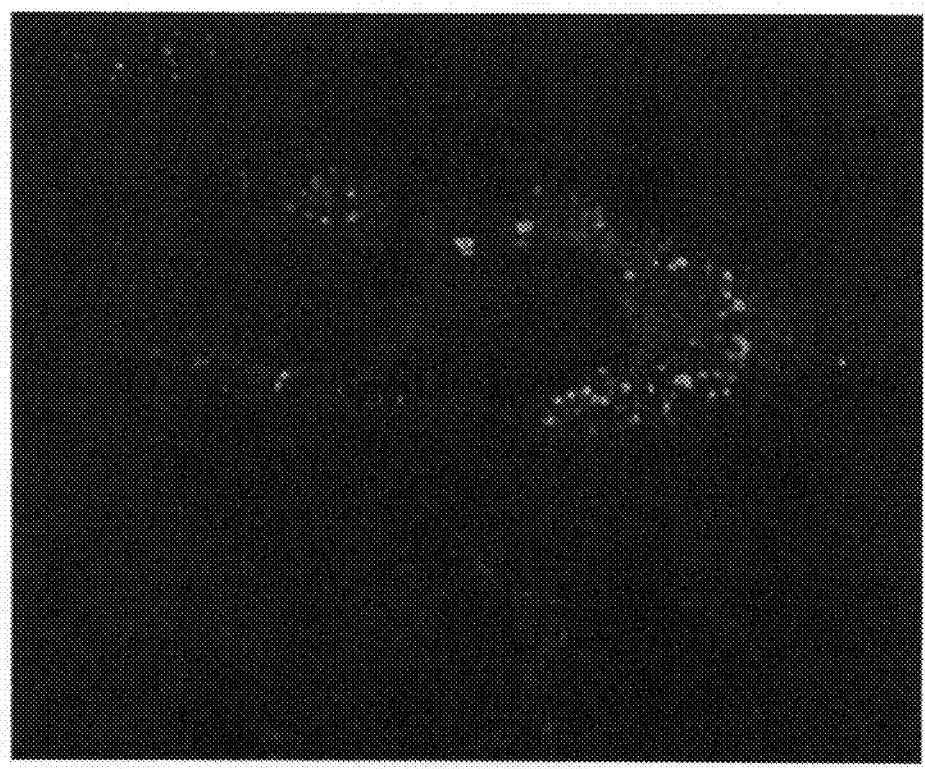
Figure 8C:
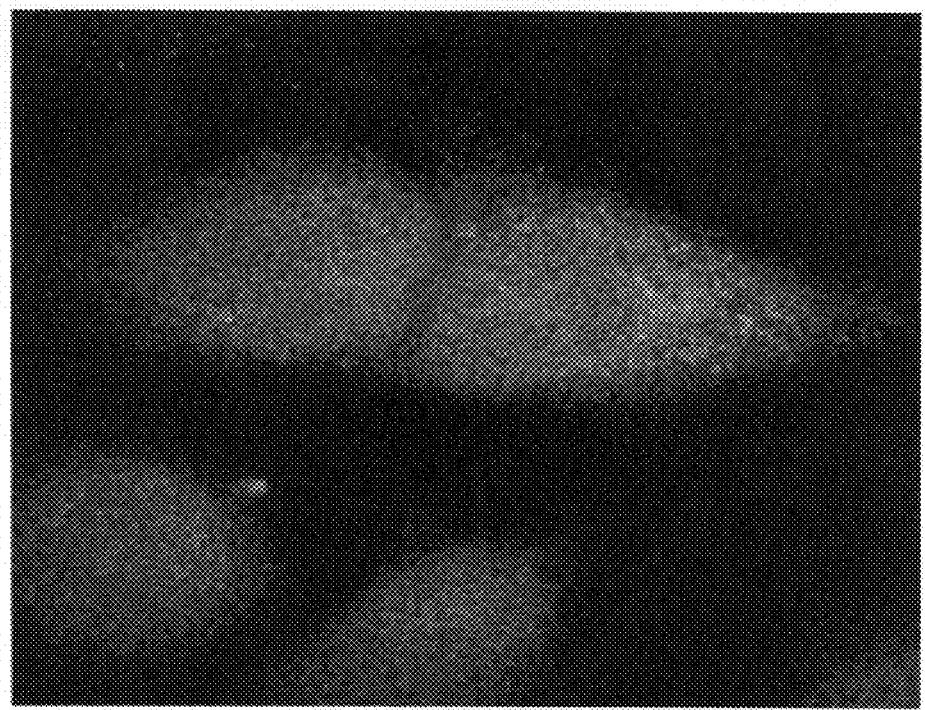
Figure 8D:
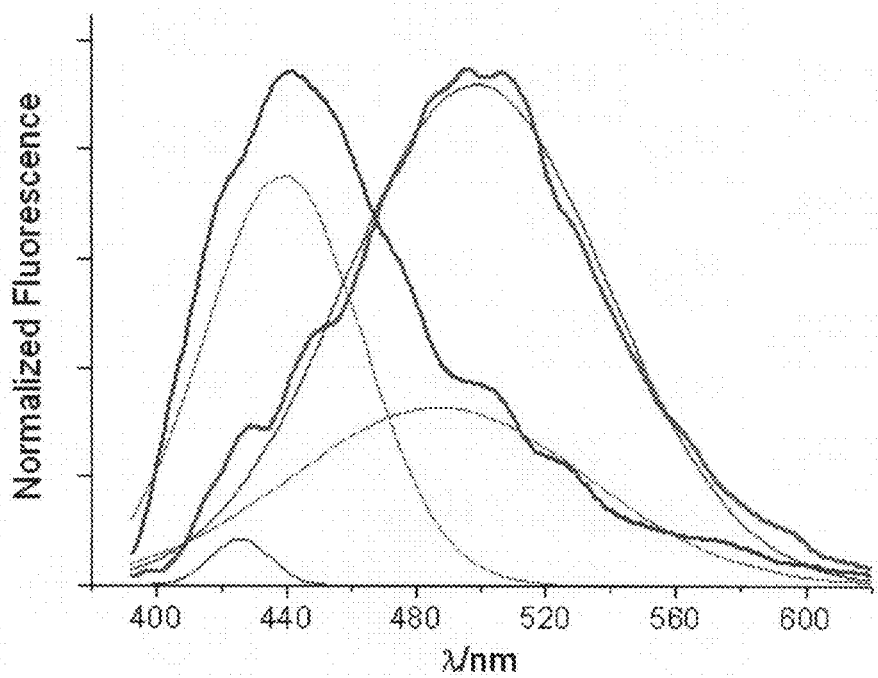
FIG. 8d shows two-photon-excited fluorescence spectra from the hydrophobic (blue) and hydrophilic (red) domains of Hep3B cells labeled with a two-photon probe of the present invention.

The TPM images of Hep3B cells labeled with the compound of Formula 13 are shown in FIGS. 8a, 8b and 8c. Because the fluorescence quantum yields of $Mg^{2+}$-the compound (Formula 7) in Tris buffer ($\phi$=0.58) and the compound of Formula 13 in DMF ($\phi$=0.32) are much higher than those of the compound of Formula 7 ($\phi$=0.04) and the compound of Formula 13 ($\phi$=0.07) in Tris buffer (Table 2), the TPEF emitted from the cells should be mostly due to the intracellular $Mg^{2+}$-the compound (Formula 7) complex or membrane bound probes. Note that the compound of Formula 13 in DMF is a good model for the latter because the $\lambda_{max}^{fl}$ values are similar (FIG. 8d). Additional evidence for this explanation was provided by the negligible TPEF emitted from the Hep3B cells labeled with the compound of Formula 13 after treatment with 10 µM calcimycin in the presence of 2 mM ethylene diamine tetraacetic acid; the fluorescence increased upon treatment with 10 µM calcimycin in the presence of 100 mM $MgCl_2$. Moreover, the images collected at 360-620 nm showed intense spots and bright domains, with TPEF maxima at λ=440 (blue) and 498 nm (red), respectively (FIG. 8d).

Compared with the emission spectra recorded in Tris buffer, the blue band was significantly blue-shifted while the red band was nearly identical (Table 2). Both spectra could be fitted to two Gaussian functions with maxima at 439 and 488 nm (pale blue lines) and at 426 and 498 nm (brown lines), respectively (FIG. 8d). It was observed that the peak positions of the dissected spectra were similar, suggesting that the probes might be located in two regions with different polarity. Furthermore, the intense spot exhibited an excited-state lifetime of 3.3 ns, which was much longer than the upper extreme of the lifetime distribution curve centered at 2.2 ns. From these results, it can be hypothesized that the probes may be located in two different environments, a more polar one that is likely to be cytosol (red emission with a shorter lifetime) and a less polar one that is likely to be membrane-associated (blue emission with a longer lifetime).

The errors arising from the membrane-bound probes could be minimized by detecting the TPEF from the intracellular $Mg^{2+}$-the compound (Formula 7) complex. As shown in FIG. 8d, the shorter-wavelength band in the dissected Gaussian function (pale blue line) decreased to the baseline at λ≈1500 nm. Thus, the TPEF emitted from the membrane-bound probe should be negligible at λ>500 nm. On the other hand, if the compound of Formula 13 in DMF is used as a model for the latter, the tail of the emission band that extends beyond 500 nm could cause an error. However, the area of the tail at λ>500 nm accounts for about 5% of the total emission band, indicating that it would not be a significant problem. Consistently, the TPEF image collected at 500-620 nm was homogeneous whereas that collected using the shorter-wavelength window of 360-460 nm clearly showed intense spots. Therefore, $Mg^{2+}$ ions could be detected in the 500-620 nm range with minimum contribution from the membrane-bound probes.

Example 8

Measurement of Intracellular free $Mg^{2+}$ in Hep3B Cells

Intracellular free $Mg^{2+}$ ion concentration ($[Mg^{2+}]$) at rest was calculated by Equation 1:

$$[Mg^{2+}] = K_d[(F-F_{min})/(F_{max}-F)] \quad (1)$$

where $K_d$ is the dissociation constant of the two-photon probe for $Mg^{2+}$, F is the observed two-photon fluorescence intensity, $F_{min}$ is the minimum fluorescence intensity, and $F_{max}$ is the maximum fluorescence intensity.

The minimum fluorescence intensity, i.e. $F_{min}$, was determined with 10 μM calcimycin in the presence of 2 mM EDTA to deplete endogenous $Mg^{2+}$. The maximum fluorescence intensity, i.e. $F_{max}$, was estimated with 10 μM calcimycin in the presence of 100 mM $MgCl_2$ (G. Farruggia, S. Iotti, L. Prodi, M. Montalti, N. Zaccheroni, P. B. Savage, V. Trapani, P. Sale, F. I. Wolf, *J. Am. Chem. Soc.* 2006, 128, 344; I. J. Reynolds, *Current Protocols in Neuroscience* Wiley: New York; 1998).

Figure 9A:
FIG. 9a is a two-photon fluorescence image of Hep3B cells labeled with a two-photon probe of the present invention.
Figure 9B:
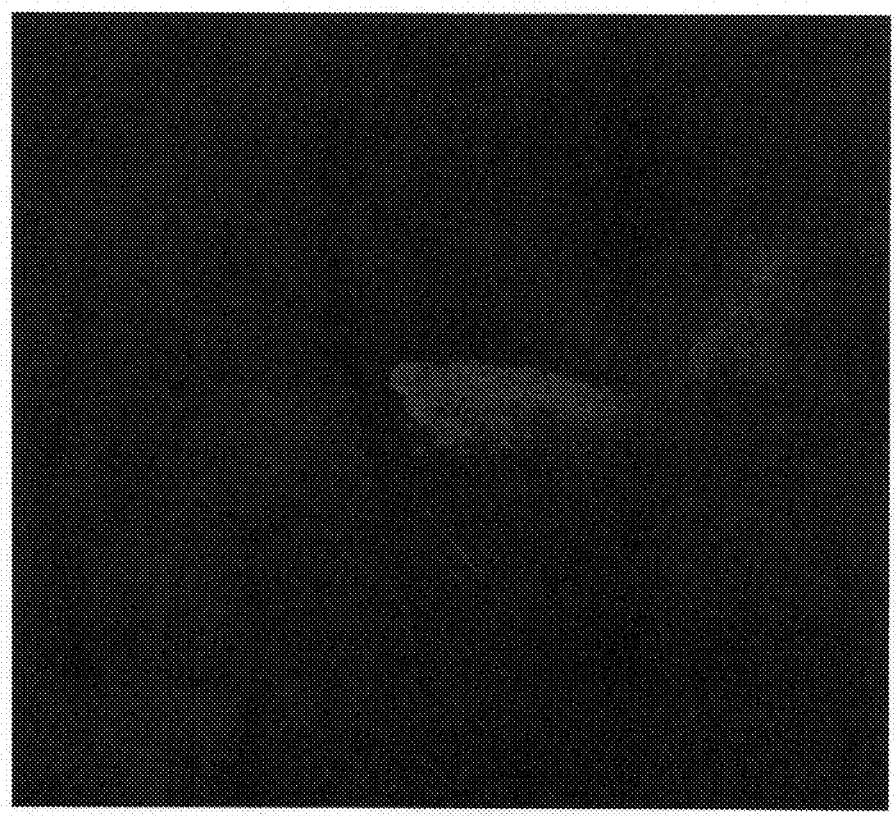
FIG. 9b is a two-photon fluorescence image of Hep3B cells treated with 10 μM calcimycin in the presence of 2 mM EDTA and labeled with a two-photon probe of the present invention.
Figure 9C:
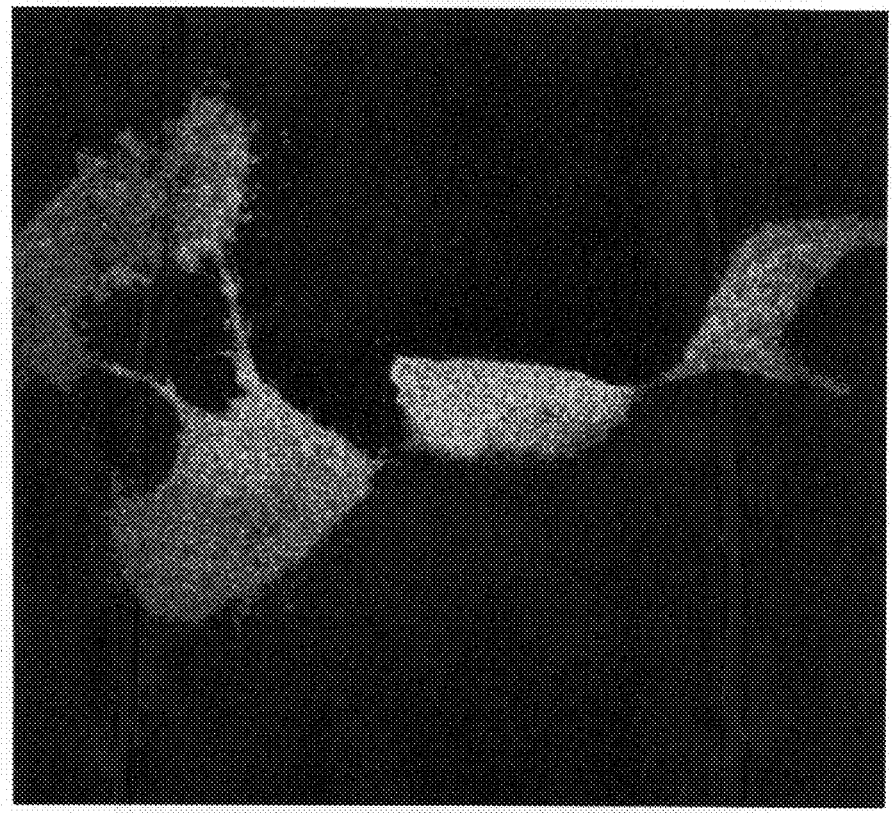
FIG. 9c is a two-photon fluorescence image of Hep3B cells treated with 10 μM calcimycin in the presence of 100 mM MgCl$_2$ and labeled with a two-photon probe of the present invention.

FIGS. 9a, 9b and 9c show a two-photon fluorescence image (9a, measurement of F) of Hep3B cells labeled with the compound (2 μM) of Formula 13, a two-photon fluorescence image (9b, measurement of $F_{min}$) of Hep3B cells treated with 10 μM calcimycin in the presence of 2 mM EDTA and labeled with the compound (2 μM) of Formula 13, and a two-photon fluorescence image (9c, measurement of $F_{max}$) of Hep3B cells treated with 10 μM calcimycin in the presence of 100 mM $MgCl_2$ and labeled with the compound (2 μM) of Formula 13.

The intracellular free $Mg^{2+}$ concentration in the resting Hep3B cells was measured to be 0.65±0.10 mM, in good agreement with the reported values (J. G. Fitz, A. H. Sostman, J. P. Middleton, *Am. J. Physiol.* (*London*) 1994, 266, G677-G684; M. R. Cho, H. S. Thatte, M. T. Silvia, D. E. Golan, *FASEB J.* 1999, 13, 677-683).

The intracellular magnesium ions have been qualitatively detected with TPM by using 2,3-dicyanohydroquinone (DCHQ), a newly developed probe (G. Farruggia, S. Iotti, L. Prodi, M. Montalti, N. Zaccheroni, P. B. Savage, V. Trapani, P. Sale, F. I. Wolf, *J. Am. Chem. Soc.* 2006, 128, 344-350). However, the present invention provides the first example of quantitative measurement of the intracellular free $Mg^{2+}$ with TPM.

Example 9

Imaging of Hippocampal Slices From Mice

Figure 10A:
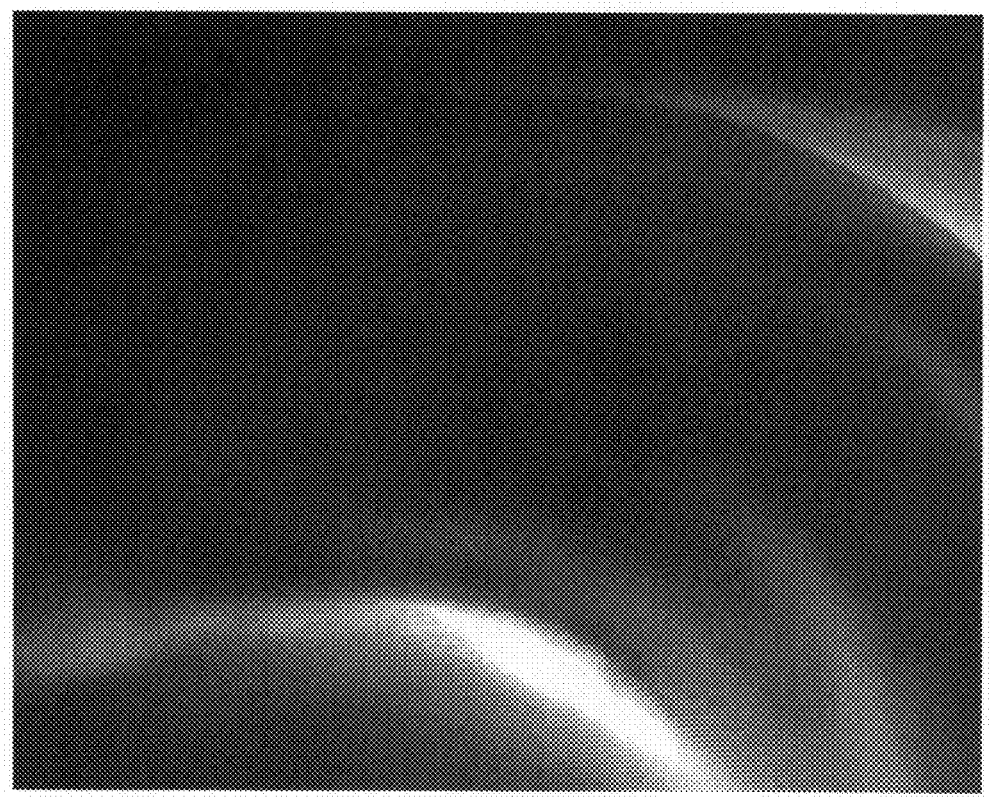
FIGS. 10a, 10b, 10c and 10d are images of an acute mouse hippocampal slice stained with a two-photon probe of the present invention. Specifically.
Figure 10B:
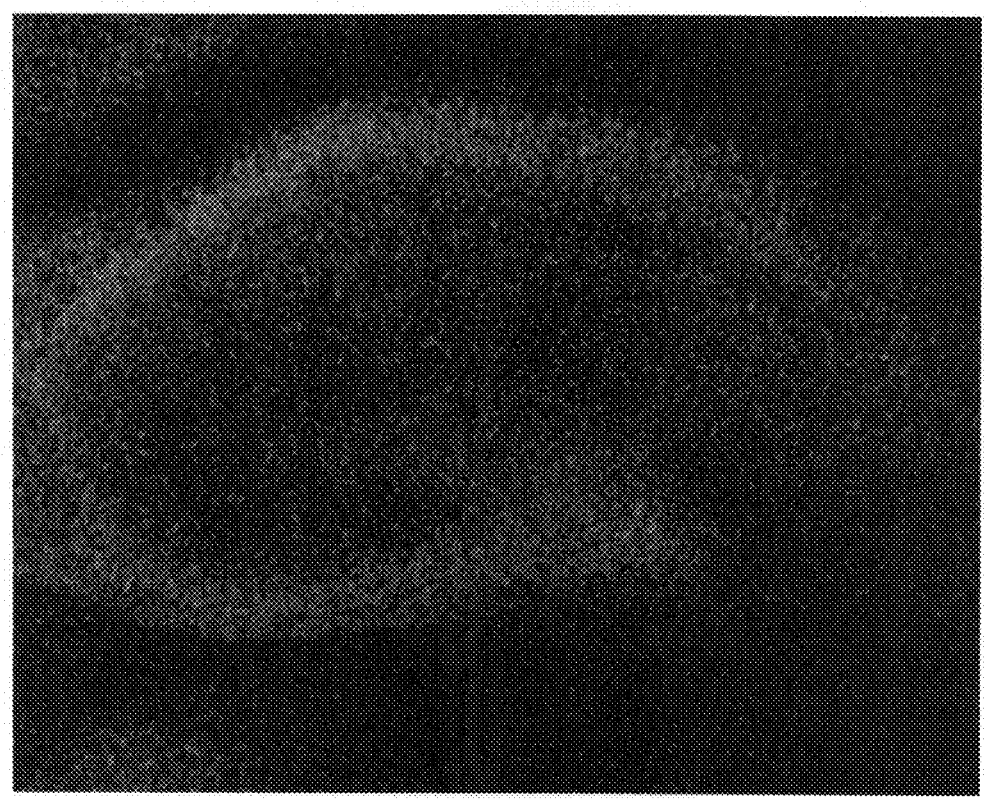
Figure 10C:
Figure 10D:

To demonstrate the utility of the two-photon probe according to the present invention in deep-tissue imaging, acute hippocampal slices from postnatal 3-day-old mice were incubated with the compound (5 μM) of Formula 13 for 30 min at 37° C. FIG. 10a displays the brightfield image of a part of an acute mouse hippocampal slice that reveals the CA1 and CA3 regions as well as the dentate gyrus upon magnification (10×). FIG. 10b displays a TPM image at the same magnification. The TPM image revealed $Mg^{2+}$ distributions in the same regions at a depth of 100-300 μm. However, the possibility cannot be ruled out that $Zn^{2+}$ may have contributed in the CA3 region. Moreover, the images (FIGS. 10c and 10d) taken at higher magnifications resolved $Mg^{2+}$ distributions in the pyramidal neuron layer of the CA1 region, where intracellular $Zn^{2+}$ is essentially nonexistent, indicating that the two-photon probe of the present invention is highly selective for $Mg^{2+}$. Furthermore, a closer examination of the image shown in FIG. 10d revealed that the probe of the present invention could also detect $Mg^{2+}$ ions in the nucleus in the deep tissue.

As apparent from the above description, the two-photon probe of the present invention is very suitable for real-time imaging of intracellular magnesium ions. The two-photon probe of the present invention shows 17-fold two-photon excited fluorescence (TPEF) enhancement in response to $Mg^{2+}$, which is 7-fold stronger than commercial probes, thus enabling staining of cells in a greatly reduced amount. In addition, the two-photon probe of the present invention has a sufficiently low molecular weight to stain cells and is very suitable for monitoring $Mg^{2+}$ ions present in the deep tissue. Furthermore, the two-photon probe of the present invention can be effectively used for the quantitative as well as qualitative detection of intracellular magnesium ions.

What is claimed is:

1. A two-photon probe for real-time monitoring of intracellular magnesium ions, represented by Formula 1:

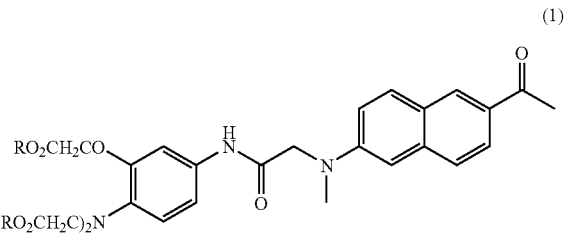

(1)

wherein R is H or $CH_2OCOCH_3$.

2. A method for preparing a two-photon probe for real-time monitoring of intracellular magnesium ions, represented by Formula 1:

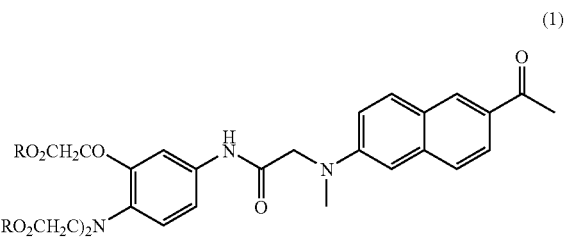

(1)

wherein R is H or CH₂OCOCH₃, the method comprising reacting 1-ethyl-3-(3-dimethylaminopropyl)carbodiimide hydrochloride, 4-dimethylaminopyridine and the compounds of Formulae 2 and 3:

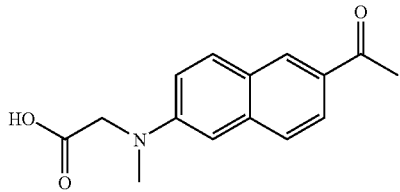
(2)

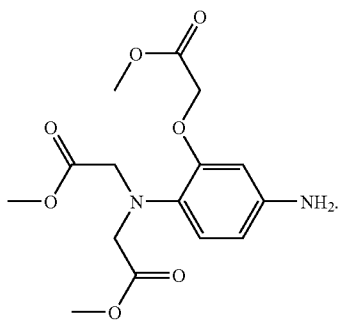
(3)

3. The method according to claim 2, wherein the compound of Formula 2 is prepared by reacting methyl bromoacetate, Na₂HPO₄, NaI and the compound of Formula 4:

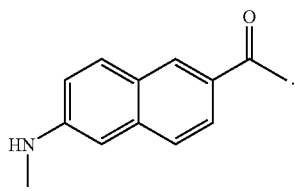
(4)

4. The method according to claim 3, wherein the compound of Formula 4 is prepared by reacting CH₃NH₂.HCl, Na₂S₂O₃, NaOH, H₂O and the compound of Formula 5:

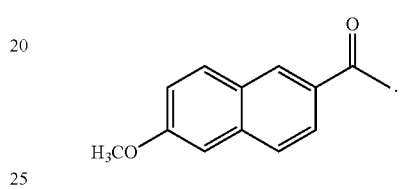
(5)

5. The method according to claim 4, wherein the compound of Formula 5 is prepared by reacting HBr with the compound of Formula 6:

(6)

6. A method for real-time monitoring of intracellular magnesium ions, the method comprising introducing the two-photon probe according to claim 1 into cells and imaging two-photon excited fluorescence emitted from the two-photon probe.

7. The method according to claim 6, wherein the two-photon excited fluorescence images are obtained in the wavelength range of 500 to 620 nm.

8. The method according to claim 6, wherein the intracellular magnesium ion concentration is quantitatively determined by Equation 1:

$$[Mg^{2+}]=K_d[(F-F_{min})/(F_{max}-F)] \quad (1)$$

where $K^d$ is the dissociation constant of the two-photon probe for $Mg^{2+}$, F is the observed two-photon fluorescence intensity, $F_{min}$ is the minimum fluorescence intensity, and $F_{max}$ is the maximum fluorescence intensity.

* * * * *